(12) United States Patent
Ock et al.

(10) Patent No.: US 12,205,288 B2
(45) Date of Patent: Jan. 21, 2025

(54) METHOD AND SYSTEM FOR ANALYZING PATHOLOGICAL IMAGE

(71) Applicant: Lunit Inc., Seoul (KR)

(72) Inventors: Chan-Young Ock, Seoul (KR);
Donggeun Yoo, Seoul (KR);
Kyunghyun Paeng, Seoul (KR)

(73) Assignee: Lunit Inc., Seoul (KR)

(*) Notice: Subject to any disclaimer, the term of this patent is extended or adjusted under 35 U.S.C. 154(b) by 0 days.

(21) Appl. No.: 18/193,275

(22) Filed: Mar. 30, 2023

(65) Prior Publication Data

US 2023/0237658 A1 Jul. 27, 2023

Related U.S. Application Data

(63) Continuation of application No. PCT/KR2022/001147, filed on Jan. 21, 2022.

(30) Foreign Application Priority Data

Jan. 22, 2021 (KR) .................. 10-2021-0009715
Jan. 13, 2022 (KR) .................. 10-2022-0005540

(51) Int. Cl.
*G06T 7/00* (2017.01)
*G06V 10/94* (2022.01)
(Continued)

(52) U.S. Cl.
CPC .......... *G06T 7/0012* (2013.01); *G06V 10/945* (2022.01); *G06V 20/695* (2022.01);
(Continued)

(58) Field of Classification Search
CPC ......... G06T 7/0012; G06T 2207/20092; G06T 2207/30096; G16H 30/20; G06V 20/695; G06V 10/945; G06V 2201/03
See application file for complete search history.

(56) References Cited

U.S. PATENT DOCUMENTS

2020/0048717 A1* 2/2020 Morrison .......... G01N 33/57492
2021/0319881 A1* 10/2021 Sasada .................. G06T 11/203
(Continued)

FOREIGN PATENT DOCUMENTS

JP 2019-525151 A 9/2019
JP 6816255 B2 1/2021
(Continued)

OTHER PUBLICATIONS

J. Wu, et al., "Deep learning approach for automated cancer detection and tumor proportion score estimation of PD-L1 expression in lung adenocarcinoma", bioRxiv, Jun. 1, 2020, pp. 1-14.
(Continued)

*Primary Examiner* — Vu Le
*Assistant Examiner* — Winta Gebreslassie
(74) *Attorney, Agent, or Firm* — Sughrue Mion, PLLC

(57) ABSTRACT

The present disclosure relates to a method, performed by at least one processor of an information processing system, of analyzing a pathological image. The method includes receiving a pathological image, detecting an object associated with medical information, in the received pathological image by using a machine learning model, generating an analysis result on the received pathological image, based on a result of the detecting, and outputting medical information about at least one region included in the pathological image, based on the analysis result.

20 Claims, 19 Drawing Sheets

(51) Int. Cl.
  *G06V 20/69* (2022.01)
  *G16H 30/20* (2018.01)

(52) U.S. Cl.
  CPC ... *G16H 30/20* (2018.01); *G06T 2207/20092* (2013.01); *G06T 2207/30096* (2013.01); *G06V 2201/03* (2022.01)

(56) References Cited

U.S. PATENT DOCUMENTS

2022/0148323 A1* 5/2022 Watanabe ............... G06T 11/00
2022/0405919 A1* 12/2022 Yip ........................ G06V 10/82

FOREIGN PATENT DOCUMENTS

| KR | 20210058210 A | * 11/2019 | ............... G06N 3/08 |
| KR | 10-2020-0077461 A | 6/2020 | |
| KR | 10-2020-0092803 A | 8/2020 | |
| WO | 2020/079667 A1 | 4/2020 | |

OTHER PUBLICATIONS

International Search Report for PCT/KR2022/001147 dated May 9, 2022 [PCT/ISA/210].

* cited by examiner

METHOD AND SYSTEM FOR ANALYZING PATHOLOGICAL IMAGE

TECHNICAL FIELD

The present disclosure relates to a method and system for analyzing a pathological image, and more particularly, to a method and system for providing medical information about a pathological image, based on an analysis result on a pathological image.

BACKGROUND ART

Cancer therapies may be classified into first-generation chemotherapies to attack not only cancer cells but also normal cells, second-generation targeted therapies to selectively attack only cancer cells, and immuno-oncology therapies to activate the immune system such that lymphocytes around cancer tissues selectively attack tumor cells. In particular, because immuno-oncology therapies generally have fewer side effects than existing cancer therapies and have a greater cancer treatment effect, the market size is steadily increasing year by year.

Meanwhile, high-cost cancer therapies may exceptionally cause side effects, and the therapeutic effects thereof may not necessarily be guaranteed for all tumors of cancer patients. In addition, while the treatment such as chemotherapy or targeted therapy causes physical and/or mental suffering for cancer patients, it is not always effective for the cancer patients. Thus, prior to subjecting a cancer patient to therapy such as immuno-oncology therapy or targeted therapy, it is important to determine whether these therapies will respond appropriately to a cancer patient, that is, whether all or at least part of the cancer patient's tumor may be removed.

Currently, programmed death-ligand 1 (PD-L1) is known as a biomarker for predicting the responsiveness of cancer patients to immunotherapy. In the existing therapy using PD-L1, tissue may be obtained from a patient before treatment, and then stained through an immunohistochemistry method. Then, the amount of expression of PD-L1 in the stained tissue is manually counted by a person, and immunotherapy is administered to a patient with a certain expression amount or higher. However, because a person directly check the PD-L1 expression, it may be difficult to obtain objective quantification due to such subjective factors.

Meanwhile, digital pathology is drawing attention as a next-generation technology for determining a patient's treatment response to anticancer drugs. Digital pathology is defined as a system and/or environment for digitizing glass slides in traditional pathology into binary files, observing, interpreting, and/or analyzing the binary files through a monitor, and then storing and managing resultant data.

DISCLOSURE

Technical Problem

The present disclosure provides a method, a computer program stored in a recording medium, and a device (system) for analyzing a pathological image.

Technical Solution

The present disclosure may be implemented in various ways, including a method, a device (system), or a computer program stored in a readable storage medium.

According to an embodiment of the present disclosure, a method, performed by at least one processor of an information processing system, of analyzing a pathological image includes receiving a pathological image, detecting an object associated with medical information, in the received pathological image by using a machine learning model, generating an analysis result on the received pathological image, based on a result of the detecting, and outputting medical information about at least one region included in the pathological image, based on the analysis result.

According to an embodiment of the present disclosure, the at least one region may be obtained by modifying, based on a user input, a region set by the at least one processor, or by modifying, by the at least one processor, a region set based on a user input.

According to an embodiment of the present disclosure, the object associated with the medical information includes at least one of a tumor cell, an immune cell, or a cancer area.

According to an embodiment of the present disclosure, the machine learning model is configured to detect programmed death-ligand 1 (PD-L1) expression on cells in the at least one region included in the pathological image.

According to an embodiment of the present disclosure, the machine learning model is trained based on training pathological images of cells which are stained by immunohistochemistry (IHC) a PD-L1 antibody, and annotation information about PD-L1 expression on at least some cells in the training pathological images.

According to an embodiment of the present disclosure, the machine learning model is configured to detect, in the at least one region included in the pathological image, at least one of a PD-L1 positive tumor cell, a PD-L1 negative tumor cell, a PD-L1 positive lymphocyte, or a PD-L1 positive macrophage.

According to an embodiment of the present disclosure, the detecting includes detecting, in the at least one region included in the pathological image, at least one of a PD-L1 positive tumor cell, a PD-L1 negative tumor cell, a PD-L1 positive lymphocyte, or a PD-L1 positive macrophage by using the machine learning model, and the generating of the analysis result includes calculating at least one of a level of PD-L1 expression in the at least one region or a level of PD-L1 expression in one or more sub-regions of the at least one region, based on the at least one of the PD-L1 positive tumor cell, the PD-L1 negative tumor cell, the PD-L1 positive lymphocyte, or the PD-L1 positive macrophage.

According to an embodiment of the present disclosure, the calculating includes identifying, among a plurality of sub-regions of the at least one region, the one or more sub-regions that satisfy a predefined criterion, and calculating a level of PD-L1 expression in the one or more sub-regions, based on the at least one of the PD-L1 positive tumor cell, the PD-L1 negative tumor cell, the PD-L1 positive lymphocyte, or the PD-L1 positive macrophage.

According to an embodiment of the present disclosure, the predefined criterion is a criterion associated with at least one of the number of tumor cells, the size of a region occupied by tumor cells, or the range of the region occupied by the tumor cells.

According to an embodiment of the present disclosure, a method, performed by at least one processor of a user terminal, of analyzing a pathological image includes transmitting a pathological image, receiving an analysis result generated based on a result of detecting, in the pathological image, an object associated with medical information, and outputting medical information about at least one region included in the pathological image, based on the analysis result.

According to an embodiment of the present disclosure, the outputting the medical information includes outputting at least one of information related to a level of PD-L1 expression in the at least one region or information related to a level of PD-L1 expression in one or more sub-regions of the at least one region.

According to an embodiment of the present disclosure, the outputting of the medical information includes outputting at least one of whether cells included in the at least one region express PD-L1, the number of PD-L1 positive tumor cells included in the at least one region, the number of PD-L1 negative tumor cells included in the at least one region, the total number of tumor cells included in the at least one region, the number of PD-L1 positive lymphocytes included in the at least one region, the number of PD-L1 positive macrophages included in the at least one region, or a level of PD-L1 expression in the at least one region.

According to an embodiment of the present disclosure, the outputting of the medical information includes outputting a PD-L1 positive tumor cell and a PD-L1 negative tumor cell in different colors.

According to an embodiment of the present disclosure, the outputting of the medical information includes outputting at least one of whether cells included in one or more sub-regions of the at least one region express PD-L1, the number of PD-L1 positive tumor cells included in the one or more sub-regions, the number of PD-L1 negative tumor cells included in the one or more sub-regions, the total number of tumor cells included in the one or more sub-regions, the number of PD-L1 positive lymphocytes included in the one or more sub-regions, the number of PD-L1 positive macrophages included in the one or more sub-regions, or a level of PD-L1 expression in one or more sub-regions.

According to an embodiment of the present disclosure, the outputting of the medical information includes outputting, at the center of each sub-region, the level of PD-L1 expression in the one or more sub-regions, by using a color corresponding to a numerical value indicated by the level of PD-L1 expression.

According to an embodiment of the present disclosure, the outputting of the medical information includes outputting at least one of a sub-region associated with a cursor displayed on the pathological image, a level of PD-L1 expression in the sub-region associated with the cursor, the number of PD-L1 positive tumor cells included in the sub-region associated with the cursor, the number of PD-L1 negative tumor cells included in the sub-region associated with the cursor, or the total number of tumor cells included in the sub-region associated with the cursor.

According to an embodiment of the present disclosure, the outputting of the medical information includes, identifying a region that satisfies a predefined criterion, among the at least one region, a plurality of sub-regions included in the at least one region, and a sub-region associated with a cursor displayed on the pathological image, and outputting information related to a level of PD-L1 expression in the region that satisfies the criterion.

According to an embodiment of the present disclosure, the predefined criterion is a criterion associated with at least one of the number of tumor cells, the size of a region occupied by tumor cells, or the range of the region occupied by the tumor cells.

According to an embodiment of the present disclosure, the at least one region may be obtained by modifying, based on a user input, a region set by the at least one processor, or by modifying, by the at least one processor, a region set based on a user input.

A computer program stored in a computer-readable recording medium is provided to execute, on a computer, the method according to an embodiment of the present disclosure.

An information processing system according to an embodiment of the present disclosure includes a memory and at least one processor connected to the memory and configured to execute at least one computer-readable program stored in the memory, and the at least one program includes instructions for receiving a pathological image, detecting an object associated with medical information, in the received pathological image by using a machine learning model, generating an analysis result on the pathological image, based on a result of the detecting, transmitting the generated analysis result to the user terminal.

A user terminal according to an embodiment of the present disclosure includes a memory and at least one processor connected to the memory and configured to execute at least one computer-readable program stored in the memory, and the at least one program includes instructions for transmitting a pathological image, receiving an analysis result generated based on a result of detecting, in the pathological image, an object associated with medical information, and outputting medical information about at least one region included in the pathological image, based on the analysis result.

Advantageous Effects

According to some embodiments of the present disclosure, objects associated with various pieces of medical information may be detected in a pathological image of a patient, and medical information may be provided based on a result of the detecting.

According to some embodiments of the present disclosure, the expression of a biomarker (e.g., programmed death-ligand 1 (PD-L1)) in at least one region included in a pathological image may be accurately detected, and accordingly, responsiveness to immunotherapy of a patient may also be accurately predicted.

According to some embodiments of the present disclosure, by calculating a level of PD-L1 expression in a region that satisfies a predefined criterion in a pathological image, a medically significant expression level of expression may be calculated, and ultimately, the accuracy of predicting responsiveness to immunotherapy of a patient may be improved.

According to some embodiments of the present disclosure, by visualizing and outputting an analysis result on a pathological image, a user receiving the result may easily and conveniently check medical information.

According to some embodiments of the present disclosure, by outputting an image/information in an environment similar to that in observing a pathological slide with a microscope, usability may be improved.

The effects of the present disclosure are not limited to the effects described above, and other effects not described will be able to be clearly understood by those of skill in the art from the description of the claims.

DESCRIPTION OF DRAWINGS

Embodiments of the present disclosure will be described with reference to the accompanying drawings described

MODE FOR INVENTION

Figure 1:
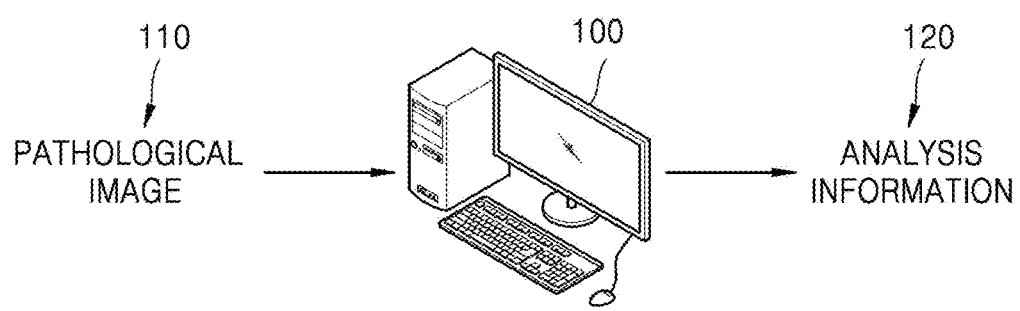
FIG. 1 is an exemplary configuration diagram illustrating an information processing system for generating an analysis result on a pathological image, according to an embodiment of the present disclosure.

Hereinafter, details for the implementation of the present disclosure will be described in detail with reference to the accompanying drawings. However, in the following description, detailed descriptions of well-known functions or configurations will be omitted when it may make the subject matter of the present disclosure rather unclear.

In the accompanying drawings, the same or corresponding elements are assigned the same reference numerals. In addition, in the following description of the embodiments, duplicate descriptions of the same or corresponding components may be omitted. However, even when descriptions of elements are omitted, it is not intended that such elements are not included in any embodiment.

Advantages and features of the disclosed embodiments and methods of accomplishing the same will be apparent by referring to embodiments described below in connection with the accompanying drawings. However, the present disclosure is not limited to the embodiments disclosed below, and may be implemented in various different forms, and the present embodiments are merely provided to make the present disclosure complete, and to fully disclose the scope of the invention to those of skill in the art to which the present disclosure pertains.

The terms used herein will be briefly described prior to describing the disclosed embodiments in detail. The terms used herein have been selected as general terms which are widely used at present in consideration of the functions of the present disclosure, and this may be altered according to the intent of an operator skilled in the art, conventional practice, or introduction of new technology. Also, in particular cases, the terms are discretionally selected by the applicant of the present disclosure, in which case, the meaning of those terms will be described in detail in the corresponding part of the detailed description. Therefore, the terms used herein are not merely designations of the terms, but the terms are defined based on the meaning of the terms and content throughout the present disclosure.

As used herein, the singular forms are intended to include the plural forms as well, unless the context clearly indicates the singular forms. Further, the plural forms are intended to include the singular forms as well, unless the context clearly indicates the plural forms. Throughout the specification, when a part "includes" a component, it means that the part may additionally include other components rather than excluding other components as long as there is no particular opposing recitation.

the term "module" or "unit" used herein refers to a software or hardware component, and "module" or "unit" performs certain roles. However, the meaning of "module" or "unit" is not limited to software or hardware. The "module" or "unit" may be configured to be in an addressable storage medium or configured to reproduce one or more processors. Accordingly, for example, the "module" or "unit" may include components such as software components, object-oriented software components, class components, and task components, and at least one of processes, functions, attributes, procedures, subroutines, program code segments of program code, drivers, firmware, micro-code, circuits, data, databases, data structures, tables, arrays, or variables. Functions provided in the components and the "modules" or "units" may be combined into a smaller number of components and "modules" or "units", or further divided into additional components and "modules" or "units".

According to an embodiment of the present disclosure, the "module" or "unit" may be implemented as a processor and a memory. The "processor" should be interpreted broadly to encompass a general-purpose processor, a central processing unit (CPU), a microprocessor, a digital signal processor (DSP), a controller, a microcontroller, a state machine, etc. Under some circumstances, the "processor" may refer to an application-specific integrated circuit (ASIC), a programmable logic device (PLD), a field-programmable gate array (FPGA), etc. The "processor" may refer to a combination of processing devices, for example, a combination of a DSP and a microprocessor, a combination of a plurality of microprocessors, a combination of one or more microprocessors in conjunction with a DSP core, or any other combination of such configurations. In addition, the "memory" should be interpreted broadly to encompass any electronic component that is capable of storing electronic information. The "memory" may refer to various types of processor-readable media such as random-access memory (RAM), read-only memory (ROM), non-volatile RAM (NVRAM), programmable ROM (PROM), erasable programmable ROM (EPROM), electrically erasable PROM (EEPROM), flash memory, a magnetic or optical data storage, registers, etc. The memory is said to be in electronic communication with a processor when the processor may read information from and/or write information to the memory. The memory integrated with a processor is in electronic communication with the processor.

In the present disclosure, the "system" may refer to at least one of a server device and a cloud device, but is not limited thereto. For example, the system may include one or more server devices. As another example, the system may include one or more cloud devices. As yet another example, the system may be configured together with both a server device and a cloud device and operated.

In the present disclosure, a 'pathological image' may refer to an image obtained by scanning a pathological slide that is fixed and stained through a series of chemical treatments in order to observe a tissue removed from a human body with a microscope. Here, the pathological image may refer to a whole slide image (WSI) including a high-resolution image of the whole slide, and may include at least one of a hematoxylin and eosin (H&E)-stained slide or an immunohistochemistry (IHC)-stained slide. The pathological image may refer to a part, for example, one or more patches, of a high-resolution whole slide image. For example, the pathological image may refer to a digital image obtained by scanning a pathological slide by using a digital scanner, and may include information about cells, tissues, and/or structures in a human body. In addition, the pathological image may include one or more patches, and histological components may be applied (e.g., tagged) to the one or more patches via an annotation operation. In the present specification, the 'pathological image' may be used interchangeably with a 'pathological slide image', a 'tissue slide image', a 'whole slide image (WSI)', and the like. Also, in the present specification, the 'pathological image' may refer to 'at least some regions included in a pathological image'.

In the present disclosure, 'IHC staining' may refer to a staining method using the principle of reacting an antibody of interest on a tissue in order to observe the presence or absence of a protein (antigen) in the nucleus, cytoplasm, or cell membrane of a tissue or cell specimen with an optical microscope. Because a product of an antigen-antibody reaction cannot be observed with a microscope as it is, a method of attaching a marker and then developing the color of the marker may be used. Examples of the color coupler for coloring the marker may include red 3-amino-9-ethylcarbazole (AEC), brown 3,3'-diaminobenzidine (DAB), or the like. In addition, in order to accurately identify the region where a protein is expressed, counterstaining with hematoxylin may be performed after treatment with the color coupler.

In the present disclosure, a 'patch' may refer to a small region in a pathological image. For example, the patch may include a region corresponding to a semantic object extracted by performing segmentation on a pathological image. As another example, the patch may refer to a combination of pixels related to histological components generated by analyzing a pathological image.

In the present disclosure, 'histological components' may include characteristics or information of cells, tissues, and/or structures in a human body included in a pathological image. Here, the characteristics of cells may include cytologic features such as a nucleus or a cell membrane. The histological components may refer to histological components of at least one patch included in the pathological image, which are inferred through a machine learning model. Meanwhile, the histological components may be obtained as a result of an annotation operation by an annotator.

In the present disclosure, 'therapy for cancer patients' may include any therapeutic agent taken by or administered to a cancer patient and/or any therapeutic treatment operated on or applied to a cancer patient. For example, therapies to be applied to cancer patients may include chemotherapies, radiotherapies, immunotherapies, and the like. In addition, the responsiveness to therapy for cancer patients may include pathological complete response, responsiveness to immuno-oncology therapy, and the like. Here, the 'pathological complete response' (hereinafter, referred to as pCR) may indicate the absence of invasive cancer in human tissue by chemotherapy or radiotherapy. For example, the pathological complete response may indicate a state in which all or at least a part of the tumor cells that were present in human tissue are removed as a result of cancer therapy.

In the present disclosure, a 'biomarker' may refer to a marker that may objectively measure a normal or pathological state, a responsiveness to a drug, and the like. Biomarkers for cancer therapy include HER2, ER, EGFR, VEGF, Bcr-Abl, ALK, Ki67, CD3, CD4, CD8, CD20, CD73, etc., and in particular, PD-L1 is a representative biomarker for cancer therapy. Recently, tumor-infiltrating lymphocytes (TILs), which are immune cells that gather around tumor tissue have been reported as new biomarkers to complement PD-L1.

In the present disclosure, a 'machine learning model' may include any model used to infer an answer to a given input. According to an embodiment, the machine learning model may include an artificial neural network model including an input layer, a plurality of hidden layers, and an output layer. Here, each layer may include one or more nodes. For example, the machine learning model may be trained to infer histological components from a pathological image and/or at least one patch included in the pathological image. In this case, histological components generated through an annotation operation may be used to train the machine learning model. As another example, the machine learning model may be trained to infer responsiveness to therapy for cancer patients, based on an interaction score, characteristics of at least one of a cell, a tissue, or a structure in a pathological image, and/or a clinical factor of a patient. In addition, the machine learning model may include weights associated with a plurality of nodes included in the machine learning model. Here, the weights may include any parameter associated with the machine learning model. In the present disclosure, a machine learning model may refer to an artificial neural network model, and an artificial neural network model may refer to a machine learning model. The machine learning model according to the present disclosure may be a model that is trained by using various learning methods. For example, various learning methods, such as supervised learning, unsupervised learning, or reinforcement learning, may be used in the present disclosure.

In the present disclosure, 'training' may refer to any process of changing a weight included in a machine learning model by using at least one patch, interaction scores, histological components, and/or clinical factors. According to an embodiment, training may refer to a process of changing or updating weights associated with a machine learning model by performing, once or multiple times, forward propagation and backward propagation on the machine learning model by using at least one patch and histological components.

In the present disclosure, 'annotation' refers to an operation of tagging a data sample with histological components, or to tagged information (i.e., an annotation) itself. Annotation may be used interchangeably with terms such as tagging or labeling, in the related art.

In the present disclosure, a 'cursor' may refer to an indicator output from a display device to indicate an input position. The position of a cursor displayed on a display may be changed in response to a movement of an input device or a user input for moving the cursor.

In the present disclosure, 'similar' may encompass sameness and similarity. For example, that two pieces of information are similar to each other may mean that the two pieces of information are the same as or similar to each other.

In the present disclosure, 'instructions' may refer to a set of instructions grouped on the basis of function, which are the components of a computer program and executable by a processor.

FIG. 1 is an exemplary configuration diagram illustrating an information processing system 100 for generating an analysis result on a pathological image 110, according to an embodiment of the present disclosure. The information processing system 100 may receive the pathological image 110 and generate an analysis result 120 on the pathological image 110. Here, the analysis result 120 and/or medical information generated based on the analysis result 120 may be used to predict responsiveness to therapy for cancer patients. Although FIG. 1 illustrates the information processing system 100 as one computing device, the present disclosure is not limited thereto, and the information processing system 100 may be configured to distribute and process information and/or data through a plurality of computing devices. In addition, although a storage system capable of communicating with the information processing system 100 is not illustrated in FIG. 1, the information processing system 100 may be configured to be connected to or communicate with one or more storage systems. The information processing system 100 may be any computing device used to generate the analysis result 120 on the pathological image 110. Here, the computing device may refer to any type of device having a computing function, and may be, for example, a notebook computer, a desktop computer, a laptop, a server, a cloud system, or the like, but is not limited thereto.

The storage system configured to be communicable with the information processing system 100 may be a device or a cloud system that stores and manages various pieces of data related to an operation of analyzing a pathological image. For efficient data management, the storage system may store and manage various types of data by using a database. Here, the various types of data may include any data related to pathological image analysis, and for example, may include the pathological image 110 and histological components about the types, positions, states, and the like of cells, tissues, and/or structures included in the pathological image 110. In addition, the various types of data may further include clinical factors, such as age, menopausal status, clinical T-stage (Clinical_T), Breast Imaging-Reporting and Data System (BIRADS), number of tumors, tumor size, Node_Enlargement, Biopsy_ER, Biopsy_PR, Biopsy_HER2, pCR_final, Pathology Type, and the like of the patient.

The information processing system 100 may receive the pathological image 110 obtained from a human tissue of a patient who is a target for predicting responsiveness to therapy for cancer patients. The pathological image 110 may be received through a communicable storage medium (e.g., a hospital system, a local/cloud storage system, etc.). The information processing system 100 may analyze the received pathological image 110 to generate the analysis result 120 on the pathological image 110. Here, the pathological image 110 may include histological components of at least one patch included in the image.

According to an embodiment, the information processing system 100 may extract histological components, which are characteristics of cells, tissues, and/or structures in the human body of the target patient, by analyzing the pathological image 110. In detail, the information processing system 100 may extract the histological components of at least one patch included in the pathological image 110 by analyzing (e.g., inferring) the pathological image 110 by using the machine learning model. For example, the histological components may include information (e.g., the number of particular cells, information about a tissue with particular cells) about cells in a patch (e.g. tumor cells, lymphocytes, macrophages, dendritic cells, fibroblasts, endothelial cells, etc.), but is not limited thereto. Here, the tumor cells may refer to cells that ignore the cell growth cycle and continue to proliferate. In particular, malignant tumor cells that infiltrate into surrounding tissues and spread and grow (metastasize) to distant tissues may be referred to as cancer cells.

According to an embodiment, the information processing system 100 may detect the expression of a biomarker in cells included in the pathological image 110, or extract, from the pathological image 110, information related to the expression of the biomarker. For example, the pathological image 110 may include an image of cells stained with an (IHC) staining technique. In addition, the information processing system 100 may extract, from the stained pathological image 110, information about positive (+) cells that express a biomarker of interest (e.g., PD-L1 positive tumor cells, PD-L1 positive lymphocytes, PD-L1 positive macrophages, etc.), and negative (−) cells that do not express the biomarker of interest (e.g., PD-L1 negative tumor cells, PD-L1 negative lymphocytes, PD-L1 negative macrophages, etc.). For example, the information processing system 100 may calculate, from the pathological image 110, a tumor proportion score (TPS) which represents the ratio of the number of PD-L1 positive tumor cells to the total number of viable tumor cells, and/or a combined positive score (CPS) which represents the ratio of the number of PD-L1 positive cells to the total number of viable tumor cells.

Another example of histological components extracted from a patch by the information processing system 100 may include information about a tissue in the patch, such as cancer epithelium, cancer stroma, normal epithelium, normal stroma, and necrosis, fat, background, and the like. Another example of histological components extracted from a patch by the information processing system 100 may include information about a structure, such as tubule formation count, tubule formation area, DCIS count, DCIS area, nerve count, nerve area, blood vessel count, blood vessel area, and the like. The histological components extracted from a patch are not limited to the above-described examples, and may include any histological components that may be quantified in the patch, such as cell instability, cell cycle, biological function, and the like.

According to an embodiment, the information processing system 100 may determine, from the pathological image 110, information about a region in which cells are arranged. For example, the information processing system 100 may extract, by using information about tissues extracted from the pathological image 110, information about a tissue in which extracted immune cells and tumor cells are located. For example, tissue information (e.g., cancer stroma, etc.) of a tissue region in which immune cells and tumor cells are located may be determined.

According to an embodiment, the histological components extracted by the information processing system 100 may be output in various forms such as region, figure, color, texture, layer, number, statistical information, text, etc. In a case in which the extracted histological components are output in color, all or at least a part of a colored region may correspond to one or more patches.

As described above, the analysis result 120 generated by the information processing system 100 and/or medical information generated and output based on the analysis result 120 may be used to infer and/or output a result of predicting responsiveness to therapy for cancer patients. In addition, by using, as additional input data, a clinical factor of the patient associated with the pathological slide received from an accessible external system, a result of predicting responsiveness to therapy for cancer patients be inferred and/or output.

Hereinafter, for a clear understanding of the present disclosure, an example of a process in which positive cells that express a biomarker of interest (e.g., PD-L1) and/or negative cells that do not express the biomarker of interest are detected in the stained pathological image, and the analysis result 120 or the medical information is generated or output based on the detected cells will be described, but the present disclosure is not limited thereto. For example, objects associated with medical information detected in the pathological image may be not only tumor cells but also various pieces of biological information. As a specific example, an object associated with medical information detected in the pathological image may be a special region included in the pathological image, such as a lesion or a cancer area, or may be information related to cells (e.g., tumor cells, immune cells, etc.), tissues, and/or structures within the human body included in the pathological image.

Figure 2:
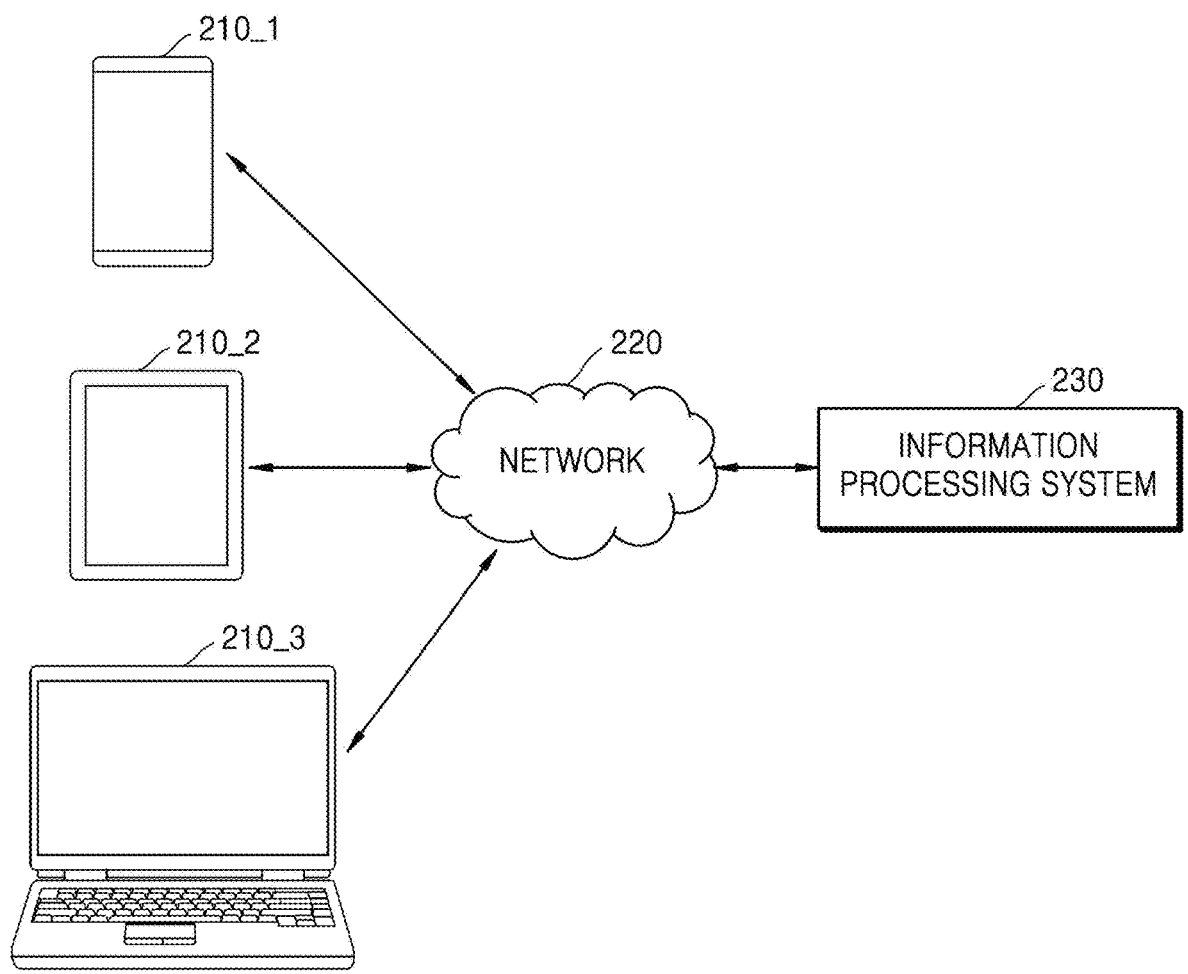
FIG. 2 is a schematic diagram illustrating a configuration in which an information processing system is communicably connected to a plurality of user terminals, according to an embodiment of the present disclosure.

FIG. 2 is a schematic diagram illustrating a configuration in which an information processing system 230 is communicably connected to a plurality of user terminals 210_1, 210_2, and 210_3, according to an embodiment of the present disclosure. As illustrated in FIG. 2, the plurality of user terminals 210_1, 210_2, and 210_3 may be connected to the information processing system 230 capable of providing a pathological image analysis service through a network 220. Here, the plurality of user terminals 210_1, 210_2, and 210_3 may include terminals of users (e.g., a doctor, a patient, etc.) to be provided with the pathological image analysis service. In an embodiment, the information processing system 230 may include one or more server devices and/or databases capable of storing, providing, and executing computer-executable programs (e.g., downloadable applications) and data related to the pathological image analysis service and the like, or one or more distributed computing devices and/or distributed databases based on cloud computing services. Also, the information processing system 230 may correspond to the information processing system 100 according to an embodiment of the present disclosure described with reference to FIG. 1.

The pathological image analysis service provided by the information processing system 230 may be provided to the user through a pathological image analysis application (e.g., a web browser application that supports pathological image analysis processing, an application dedicated to pathological image analysis, etc.) installed in each of the plurality of user terminals 210_1, 210_2, and 210_3. For example, the information processing system 230 may provide information corresponding to an analysis request on a pathological image received from the user terminals 210_1, 210_2, and 210_3 through the pathological image analysis application, or perform a process corresponding to the analysis request.

The plurality of user terminals 210_1, 210_2, and 210_3 may communicate with the information processing system 230 through the network 220. The network 220 may be configured to enable communication between the plurality of user terminals 210_1, 210_2, and 210_3 and the information processing system 230. The network 220 may be configured as, for example, a wired network such as Ethernet, a wired home network (e.g., power line communication), a telephone line communication device, or Recommended Standard (RS)-serial communication, a wireless network such as a mobile communication network, a wireless local area network (WLAN), Wi-Fi, Bluetooth, or ZigBee, or a combination thereof, according to an installation environment. The communication method is not limited, and may include short-range wireless communication between the user terminals 210_1, 210_2, and 210_3, as well as a communication method utilizing a communication network that the network 220 may include (e.g., a mobile communication network, wired Internet, wireless Internet, a broadcasting network, a satellite network, etc.).

Although the mobile phone terminal 210_1, the tablet terminal 210_2, and the personal computer (PC) terminal 210_3 are illustrated in FIG. 2 as examples of user terminals, the present disclosure is not limited thereto, and the user terminals 210_1, 210_2, and 210_3 may be any computing devices capable of performing wired and/or wireless communication and executing the pathological image analysis application or the like installed therein. For example, the user terminal may include a smart phone, a mobile phone, a navigation device, a computer, a notebook computer, a digital broadcasting terminal, a personal digital assistant (PDA), a portable multimedia player (PMP), a tablet PC, a game console, an artificial intelligence (AI) speaker, a wearable device, an internet-of-things (IoT) device, a virtual reality (VR) device, an augmented reality (AR) device, a set-top box, and the like. In addition, although FIG. 2 illustrates that three user terminals 210_1, 210_2, and 210_3 communicate with the information processing system 230 through the network 220, the present disclosure is not limited thereto, and a different number of user terminals may be configured to communicate with the information processing system 230 through the network 220.

According to an embodiment, the information processing system 230 may receive, from the plurality of user terminals 210_1, 210_2, and 210_3, a pathological image and/or an analysis request on the pathological image. Then, the information processing system 230 may generate an analysis result based on the received pathological image, and provide the analysis result to the plurality of user terminals 210_1, 210_2, and 210_3.

Figure 3:
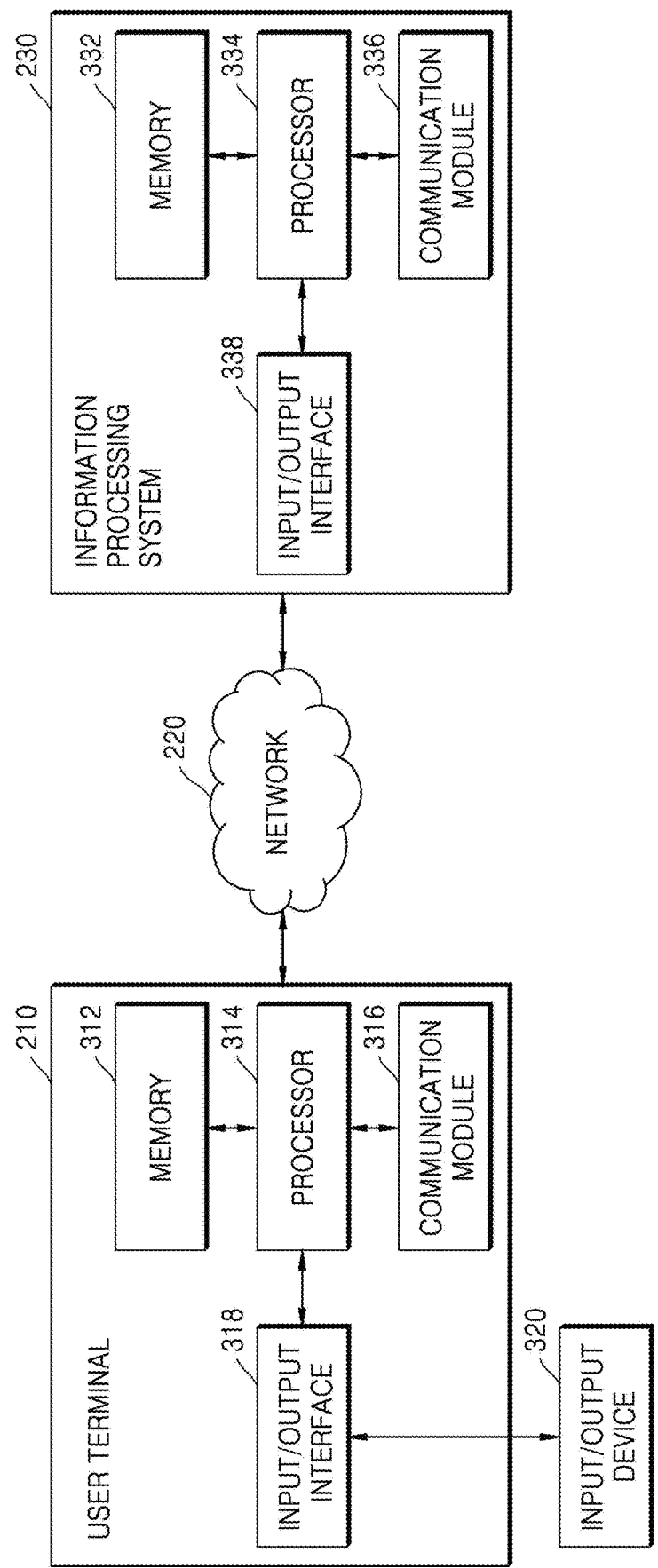
FIG. 3 is a block diagram illustrating an internal configuration of a user terminal and an information processing system, according to an embodiment of the present disclosure.

FIG. 3 is a block diagram illustrating an internal configuration of a user terminal 210 and the information processing system 230, according to an embodiment of the present disclosure. The user terminal 210 may refer to any computing device capable of executing a pathological image analysis application or the like and performing wired/wireless communication, and for example, may include the mobile phone terminal 210_1, the tablet terminal 210_2, and the PC terminal 210_3 of FIG. 2. As illustrated in FIG. 3, the user terminal 210 may include a memory 312, a processor 314, a communication module 316 and an input/output interface 318. Similarly, the information processing system 230 may include a memory 332, a processor 334, a communication module 336 and an input/output interface 338. As illustrated in FIG. 3, the user terminal 210 and the information processing system 230 may be configured to communicate information and/or data through the network 220 by using the respective communication modules 316 and 336. In addition, an input/output device 320 may be configured to input information and/or data to the user terminal 210 through the input/output interface 318, or output information and/or data generated by the user terminal 210. Although FIG. 3 illustrates that the input/output device 320 is outside the user terminal 210, but the present disclosure is not limited thereto. For example, the input/output device 320 may be an integral part and/or a part of the user terminal 210, or may be an external device connected to the user terminal 210 in a wired or wireless manner.

The memories 312 and 332 may include any non-transitory computer-readable recording medium. According to an embodiment, the memories 312 and 332 may include a permanent mass storage device, such as random-access memory (RAM), read-only memory (ROM), a disk drive, a solid-state drive (SSD), or flash memory. As another example, the permanent mass storage device, such as ROM, an SSD, flash memory, or a disk drive, may be included in the user terminal 210 or the information processing system 230, as a separate permanent storage device distinguished from a memory. In addition, the memories 312 and 332 may store an operating system and at least one piece of program code (e.g., code for the pathological image analysis application that is installed in and executed by the user terminal 210).

Such software components may be loaded from a computer-readable recording medium separate from the memories 312 and 332. The separate computer-readable recording medium may include a recording medium that may be directly connected to the user terminal 210 and the information processing system 230, and may include, for example, a computer-readable recording medium such as a floppy drive, a disk, a tape, a digital video disc (DVD)/compact disc ROM (CD-ROM) drive, or a memory card. As another example, the software components may also be loaded into the memories 312 and 332 via the communication module rather than a computer-readable recording medium. For example, at least one program may be loaded into the memories 312 and 332, based on a computer program installed by files provided by developers or a file distribution system that distributes application installation files through the network 220.

The processors 314 and 334 may be configured to process commands of a computer program by performing basic arithmetic, logic, and input/output operations. The commands may be provided to the processors 314 and 334 by the memories 312 and 332 or the communication modules 316 and 336. For example, the processors 314 and 334 may be configured to execute commands received according to program code stored in a recording device such as the memories 312 and 332.

The communication modules 316 and 336 may provide configurations or functions for the user terminal 210 and the information processing system 230 to communicate with each other through the network 220, and may provide configurations or functions for the user terminal 210 and/or the information processing system 230 to communicate with other user terminals or other systems (e.g., a separate cloud system). For example, a request or data (e.g., a pathological image and/or an analysis request on the pathological image, etc.) generated by the processor 314 of the user terminal 210 according to program code stored in a recording device, such as the memory 312, may be transmitted to the information processing system 230 through the network 220 under control by the communication module 316. Conversely, a control signal or a command provided under control by the processor 334 of the information processing system 230 may be received by the user terminal 210 through the communication module 316 of the user terminal 210 via the communication module 336 and the network 220. For example, the user terminal 210 may receive an analysis result on a pathological image, from the information processing system 230 through the communication module 316.

The input/output interface 318 may be a unit for interfacing with the input/output device 320. For example, the input device may include a device such as a camera, a keyboard, a microphone, a mouse, etc. including an audio sensor and/or an image sensor, and the output device may include a device such as a display, speaker, a haptic feedback device, etc. As another example, the input/output interface 318 may be a unit for interfacing with a device in which a configuration or a function for performing input and output is integrated, such as a touch screen. For example, when the processor 314 of the user terminal 210 processes a command of a computer program loaded into the memory 312, a service screen or the like configured by using information and/or data provided by the information processing system 230 or other user terminals may be displayed on a display through the input/output interface 318. In addition, the input/output interface 338 of the information processing system 230 may be a unit for interfacing with a device (not shown) for input or output that may be connected to or included in the information processing system 230. Although FIG. 3 illustrates that the input/output interfaces 318 and 338 are separate elements from the processors 314 and 334, but the present disclosure is not limited thereto, and the input/output interfaces 318 and 338 may be included in the processors 314 and 334, respectively.

The user terminal 210 and the information processing system 230 may include more components than those illustrated in FIG. 3. According to an embodiment, the user terminal 210 may be implemented to include at least a part of the input/output device 320. In addition, the user terminal 210 may further include other components, such as a transceiver, a global positioning system (GPS) module, a camera, various sensors, a database, etc. For example, in a case in which the user terminal 210 is a smart phone, the user terminal 210 may include components that are generally included in a smart phone, and for example, may be implemented to further include various components such as an acceleration sensor, a gyro sensor, a camera module, various physical buttons, a button using a touch panel, input and output ports, a vibrator for vibration, etc. According to an embodiment, the processor 314 of the user terminal 210 may be configured to execute a pathological image analysis application or the like. In this case, code associated with the application and/or program may be loaded into the memory 312 of the user terminal 210.

While a program for the pathological image analysis application is running, the processor 314 may receive a text, an image, a video, an audio, and/or an motion that is input or selected through an input device connected to the input/output interface 318, such as a touch screen, a keyboard, a camera including an audio sensor and/or an image sensor, or a microphone, and may store the received text, image, video, audio, and/or motion in the memory 312 or provide the received text, image, video, audio, and/or motion to the information processing system 230 through the communication module 316 and the network 220. For example, the processor 314 may receive an input for selecting a pathological image by the user, and provide the received input to the information processing system 230 through the communication module 316 and the network 220. As another example, the processor 314 may receive a user input for requesting analysis of the selected pathological image, and provide the received user input to the information processing system 230 through the communication module 316 and the network 220. As another example, the processor 314 may receive a user input for inputting a clinical factor through the input/output device 320, and provide data related to the clinical factor, to the information processing system 230 through the network 220 and the communication module 316.

The processor 314 of the user terminal 210 may be configured to manage, process, and/or store information and/or data received from the input/output device 320, other user terminals, the information processing system 230, and/or a plurality of external systems. Information and/or data processed by the processor 314 may be provided to the information processing system 230 through the communication module 316 and the network 220. The processor 314 of the user terminal 210 may transmit and output information and/or data to the input/output device 320 through the input/output interface 318. For example, the processor 314 may display received information and/or data on a screen of a user terminal.

The processor 334 of the information processing system 230 may be configured to manage, process, and/or store information and/or data received from a plurality of user terminals 210 and/or a plurality of external systems. Information and/or data processed by the processor 334 may be provided to the user terminal 210 through the communication module 336 and the network 220. In an embodiment, the processor 334 of the information processing system 230 may generate an analysis result on a received pathological image, based on a pathological image analysis request received from the user terminal 210.

The processor 334 of the information processing system 230 may be configured to output processed information and/or data through the input/output device 320 of the user terminal 210, such as a device capable of outputting a display (e.g., a touch screen, a display, etc.) or a device capable of outputting a sound (e.g., a speaker). In an embodiment, the processor 334 of the information processing system 230 may be configured to provide the generated analysis result to the user terminal 210 through the communication module 336 and the network 220, and output the analysis result through the device capable of outputting a display or the like of the user terminal 210. Here, the analysis result may include medical information generated based on the analysis result.

Figure 4:
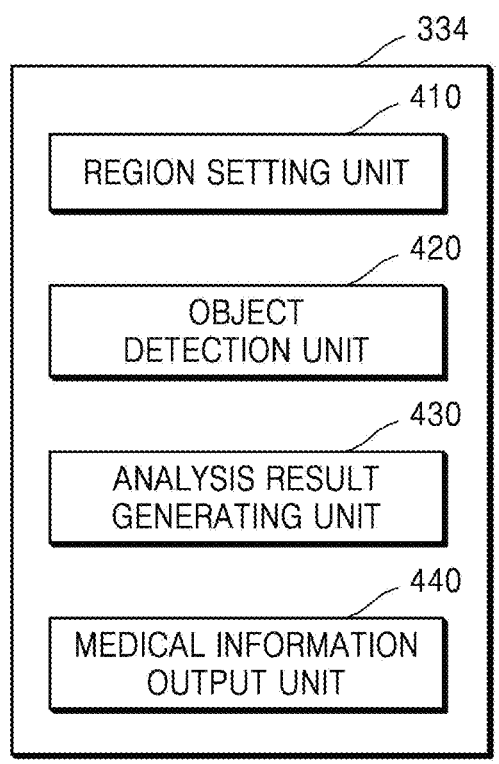
FIG. 4 is a diagram illustrating an internal configuration of a processor of an information processing system according to an embodiment of the present disclosure.

FIG. 4 is a diagram illustrating an internal configuration of the processor 334 of the information processing system according to an embodiment of the present disclosure. According to an embodiment, the processor 334 may include a region setting unit 410, an object detection unit 420, an analysis result generating unit 430, and a medical information output unit 440. Although the internal components of the processor 334 are described separately from each other according to their functions with reference to FIG. 4, this does not necessarily mean that they are physically separated from each other. In addition, the internal components of the processor 334 illustrated in FIG. 4 are only examples, and are not the essential components. Thus, in some embodiments, the processor 334 may be implemented differently, such as further including components other than the illustrated internal components, or omitting some of the illustrated internal components.

The processor 334 may receive a pathological image obtained from a human tissue of a patient who is a target for predicting responsiveness to therapy for cancer patients. Here, the pathological image may include histological components of at least one patch included in the image. According to an embodiment, the pathological image may be received through a communicable storage medium (e.g., a hospital system, a local/cloud storage system, etc.), a user terminal, or the like.

The region setting unit 410 may set a region to be analyzed in the pathological image. According to an embodiment, the region setting unit 410 may set the region to be analyzed, by using a machine learning model. Here, the machine learning model may be a model trained to receive a pathological image and infer a region to be analyzed in the pathological image. According to another embodiment, the region setting unit 410 may set a region to be analyzed, based on an input of a user (e.g., a doctor, a pathologist, a medical specialist or a patient receiving a pathological image analysis service).

For example, the region setting unit 410 may receive a user input for selecting at least a partial region of the pathological image, and set, as the region to be analyzed, a region associated with the selected region.

As another example, the region setting unit 410 may receive a user input for selecting at least a partial region of the pathological image, and set the region to be analyzed, by modifying the at least a partial region selected by the user. In detail, the region setting unit 410 may receive a user input for selecting at least a partial region of the pathological image, modify, based on information related to tissues and/or structures in the human body included in the pathological image, the region selected by the user, and finally set the modified region as the region to be analyzed. For example, at least a part of the region selected by the user may be modified such that the contour of the modified region is the same as or similar to the contour of a tissue region and/or a structure region in the human body.

As another example, the region to be analyzed may be a region obtained by modifying, based on an input of the user, a region to be analyzed that is inferred by the machine learning model. In detail, the region to be analyzed that is inferred by the machine learning model may be transmitted to a user terminal, and then displayed on a screen of the user terminal, and the user may modify at least a part of the inferred region to be analyzed. The region setting unit 410 may receive a user input for modifying at least a part of the inferred region to be analyzed, and finally set the modified region as the region to be analyzed.

The object detection unit 420 may detect, in the pathological image, an object associated with medical information. The object associated with medical information detected in the pathological image may be various types of biological information. For example, the object associated with medical information detected in the pathological image may be a medically significant region included in the pathological image, such as a lesion or a cancer area, or information related to cells (e.g., tumor cells, immune cells, etc.), tissues, and/or structures in the human body included in the pathological image. As a specific example, the object detection unit 420 may detect, in a stained pathological image, positive cells that express a biomarker of interest, and negative cells that do not express the biomarker of interest.

According to an embodiment, the object detection unit 420 may detect PD-L1 expression on cells in at least some regions included in the pathological image, by using a machine learning model. For example, the object detection unit 420 may detect PD-L1 positive tumor cells, PD-L1 negative tumor cells, and the like, in at least some regions of the pathological image by using the machine learning model. As another example, the object detection unit 420 may detect at least one of PD-L1 positive tumor cells, PD-L1 negative tumor cells, PD-L1 positive lymphocytes, or PD-L1 positive macrophages, in at least some regions of the pathological image by using the machine learning model. Here, the machine learning model may include a detector for detecting the above-described objects.

The machine learning model used by the object detection unit 420 to detect an object associated with medical information may be a model trained based on training pathological images and annotation information about the training pathological images. In an embodiment, the machine learning model may be a model trained based on training pathological images of cells which are IHC-stained by using a PD-L1 antibody and annotation information about PD-L1 expression in at least some of the training pathological images. Here, the annotation information about PD-L1 expression may include values within a continuous range, values according to a preset grade, range, or reference, etc. Annotation may be performed in various ways, such as pixel level, region level, or image level. For example, the machine learning model may be a model trained based on training pathological images of cells which are IHC-stained by using a PD-L1 antibody, and annotation information about at least one of PD-L1 positive tumor cells, PD-L1 negative tumor cells, PD-L1 positive lymphocytes, or PD-L1 positive macrophages in the training pathological images.

The analysis result generating unit 430 may generate various analysis results associated with medical information, based on objects detected in at least some regions of the pathological image. According to an embodiment, the analysis result generating unit 430 may calculate various numerical values associated with medical information, such as the number of PD-L1 positive tumor cells, the number of PD-L1 negative tumor cells, the total number of tumor cells, the number of PD-L1 positive lymphocytes, the number of PD-L1 positive macrophages included in at least some regions included in the pathological image, the level of PD-L1 expression of the at least some regions (e.g. a TPS, a CPS, etc.). For example, the analysis result generating unit 430 may calculate a TPS for at least some regions included in the pathological image, based on PD-L1 positive tumor cells and PD-L1 negative tumor cells detected in the at least some regions. The TPS may be calculated according to Equation 1 below.

$$TPS = \frac{\text{Number of } PD-L1 \text{ positive tumor cells}}{\text{Number of viable tumor cells}} \times 100(\%) \quad \text{[Equation 1]}$$

Depending on the calculated TPS, the level of PD-L1 expression may be classified. In detail, the level of PD-L1 expression may be classified as 'no PD-L1 expression' when TPS<1%, 'PD-L1 expression is present' when 1%≤TPS<50%, and 'PD-L1 expression is high' when TPS≥50%. However, cut-off values for classifying the range of TPS are not limited thereto, and the cut-off values may vary depending on the type of carcinoma, the type of PD-L1 antibody, and the like.

As another example of calculating the level of PD-L1 expression, the analysis result generating unit 430 may calculate a CPS for at least some regions included in the pathological image, based on PD-L1 positive tumor cells, PD-L1 negative tumor cells, PD-L1 positive lymphocytes, and PD-L1 positive macrophages detected in the at least some regions. The CPS can be calculated according to Equation 2 below.

$$CPS = \frac{\begin{array}{c}\text{Number of } PD-L1 \text{ positive tumor cells,}\\ PD-L1 \text{ positive lymphocytes,}\\ PD-L1 \text{ positive macrophages}\end{array}}{\text{Number of viable tumor cells}} \times 100(\%) \quad \text{[Equation 2]}$$

Depending on the calculated CPS, the level of PD-L1 expression may be classified. In detail, the calculated CPS may be classified, with a cut-off value of 10%, into a group of CPS≥10% and a group of CPS<10%, but the present disclosure is not limited thereto, and the cut-off value may vary depending on the type of carcinoma, the type of PD-L1 antibody, and the like.

According to an embodiment, the analysis result generating unit 430 may divides the entire region or at least some regions of the pathological image into a plurality of sub-regions according to a predefined criterion, and may calculate various numerical values associated with medical information for each of the plurality of sub-regions. Here, the predefined criterion may be a medically determined or discovered criterion, a criterion derived through a machine learning model, or an arbitrarily defined criterion. For example, the predefined criterion may include at least one of the number of tumor cells included in a certain region, the size of a region occupied by tumor cells, or the range of the region occupied by the tumor cells.

According to an embodiment, the analysis result generating unit 430 may divide the entire region or at least some regions of the pathological image into a plurality of circular sub-regions having the same size, and may calculate various numerical values associated with medical information for one or more sub-regions. For example, the various numerical values may include the number of PD-L1 positive tumor cells, the number of PD-L1 negative tumor cells, the total number of tumor cells, the number of PD-L1 positive lymphocytes, the number of PD-L1 positive tumor cells, the number of PD-L1 positive macrophages included in one or more sub-regions, a sub-TPS and a sub-CPS as the level of PD-L1 expression in one or more sub-regions, etc. In addition, the plurality of circular sub-regions may have the same shape and/or size as a region viewed by pathologists observing the pathological slide with an actual microscope. Also, the plurality of sub-regions may overlap.

Meanwhile, in order to calculate a clinically significant level of PD-L1 expression, it may be desirable to use a pathological image in which a sufficient number of tumor cells is present or the size or range of a region occupied by tumor cells satisfies a predefined criterion. That is, even within the pathological image, the level of PD-L1 expression in a region in which the number of tumor cells and the size or range of a region occupied by tumor cells satisfy a certain level may be considered valid.

According to an embodiment, the analysis result generating unit 430 may identify at least one region that satisfies a predefined criterion, and calculate the level of PD-L1 expression in the region(s) that satisfies the criterion. For example, the predefined criterion may be a criterion associated with at least one of the number of tumor cells included in a certain region, the size of a region occupied by tumor cells, or the range of the region occupied by the tumor cells. In this case, when determining the size or range of a region occupied by tumor cells, a region of necrosis or non-viable tumor cells may be excluded. As a specific example, the predefined criterion may be 'at least 100 tumor cells'. However, the predefined criterion is not limited thereto, and may vary depending on the type of PD-L1 antibody used for IHC staining.

The medical information output unit 440 may be configured to output, through an output device (e.g., a display, etc.) of a user terminal, the analysis result on the pathological image generated by the region setting unit 410, the cell detection unit 420, and/or the analysis result generating unit 430, and/or medical information generated based on the analysis result. For example, the medical information output unit 440 may provide the generated analysis result and/or medical information to the user terminal, and the analysis result and/or medical information may be output through a screen of the user terminal. Here, the medical information may include various pieces of information that may be obtained from the pathological image. For example, the medical information may include not only a quantified numerical value that may be obtained from the pathological image, but also information obtained by visualizing the numerical value, predictive information according to the numerical value, image information, statistical information, and the like. An example in which the generated analysis result and/or medical information is output through the output device of the user terminal will be described below in detail with reference to FIGS. 7 to 14.

At least some of the processes described as being performed by the processor 334 of the information processing system may be performed by a processor of the user terminal. For example, at least a part of the analysis result and/or the medical information generated by the processor 334 of the information processing system may be generated by the user terminal.

Figure 5:
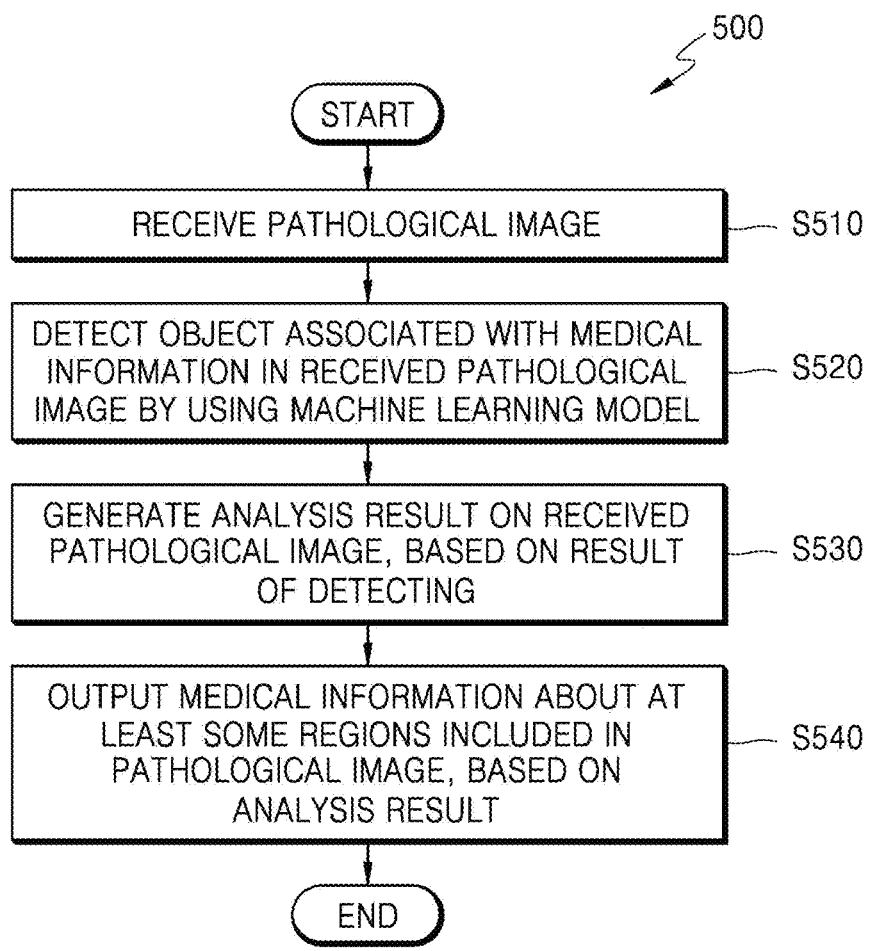
FIG. 5 is a flowchart illustrating an example of a method of analyzing a pathological image according to an embodiment of the present disclosure.

FIG. 5 is a flowchart illustrating an example of a method 500 of analyzing a pathological image according to an embodiment of the present disclosure. The method 500 may be initiated when a processor (e.g., at least one processor of an information processing system) receives a pathological image (S510).

Then, the processor may detect an object associated with medical information in the received pathological image by using a machine learning model (S520). The object associated with medical information detected in the pathological image may be various types of biological information. For example, the object associated with medical information detected in the pathological image may be a medically significant region included in the pathological image, such as a lesion or a cancer area, or information related to cells (e.g., tumor cells, immune cells, etc.), tissues, and/or structures in the human body included in the pathological image. As a specific example, the processor may detect, in a stained pathological image, positive cells that express a biomarker of interest, and negative cells that do not express the biomarker of interest.

According to an embodiment, the machine learning model may be configured to detect PD-L1 expression on cells in at least some regions included in a pathological image. Here, the machine learning model may be a model trained based on training pathological images of cells which are IHC-stained by using a PD-L1 antibody and annotation information about PD-L1 expression on at least some cells in training the pathological images. In an embodiment, the processor may detect at least one of PD-L1 positive tumor cells, PD-L1 negative tumor cells, PD-L1 positive lymphocytes, or PD-L1 positive macrophages, by using the machine learning model configured to detect PD-L1 expression on cells in at least some regions included in a pathological image.

Then, the processor may generate an analysis result on the received pathological image, based on a result of the detecting (S530). For example, the processor may calculate the level of PD-L1 expression in at least some regions and/or the level of PD-L1 expression in one or more sub-regions of at least some regions, based on at least one of the detected PD-L1 positive tumor cells, PD-L1 negative tumor cells, PD-L1 positive lymphocytes, or PD-L1 positive macrophages.

Additionally or alternatively, the processor may identify at least one of the plurality of sub-regions that satisfies a predefined criterion, and calculate the level of PD-L1 expression in the identified at least one sub-region, based on at least one of PD-L1 positive tumor cells, PD-L1 negative tumor cells, PD-L1 positive lymphocytes, or PD-L1 positive macrophages. Here, the predefined criterion may be a criterion associated with at least one of the number of tumor cells, the size of a region occupied by tumor cells, or the range of the region occupied by the tumor cells.

According to an embodiment, the region to be analyzed may include at least one of a region set by the processor, a region set based on a user input, a region obtained by modifying, based on a user input, a region set by the processor, or a region obtained by modifying, by the processor, a region set based on a user input. For example, the processor may set a region to be analyzed, by using a machine learning model. Here, the machine learning model may be a model trained to receive a pathological image and infer a region to be analyzed in the pathological image.

As another example, the processor may set a region to be analyzed, based on an input of a user (e.g., a doctor or a patient receiving a pathological image analysis service). As a specific example of setting a region to be analyzed based on a user input, the processor may receive a user input for selecting at least a partial region of the pathological image, and set, as the region to be analyzed, a region associated with the selected region.

As another example, the processor may receive a user input for selecting at least a partial region of the pathological image, and set the region to be analyzed, by modifying the at least a partial region selected by the user. In detail, the processor may receive a user input for selecting at least a partial region of the pathological image, modify, based on information related to tissues and/or structures in the human body included in the pathological image, the region selected by the user, and finally set the modified region as the region to be analyzed. For example, at least a part of the region selected by the user may be modified such that the contour of the modified region is the same as or similar to the contour of a tissue region and/or a structure region in the human body.

As another example, the region to be analyzed may be a region obtained by modifying, based on an input of the user, a region to be analyzed that is inferred by the machine learning model. In detail, the region to be analyzed that is inferred by the machine learning model may be transmitted to a user terminal, and then displayed on a screen of a user terminal, and the user may modify at least a part of the inferred region to be analyzed. The processor may receive a user input for modifying at least a part of the inferred region to be analyzed, and finally set the modified region as the region to be analyzed.

Then, the processor may output medical information about at least some regions included in the pathological image, based on the analysis result (S540). For example, the processor may provide the generated analysis result and/or medical information to the user terminal, and the analysis result and/or medical information may be output or displayed through a screen of the user terminal. Here, the medical information may include various pieces of information that may be obtained from the pathological image. For example, the medical information may include not only a quantified numerical value that may be obtained from the pathological image, but also information obtained by visualizing the numerical value, predictive information according to the numerical value, image information, statistical information, and the like.

Figure 6:
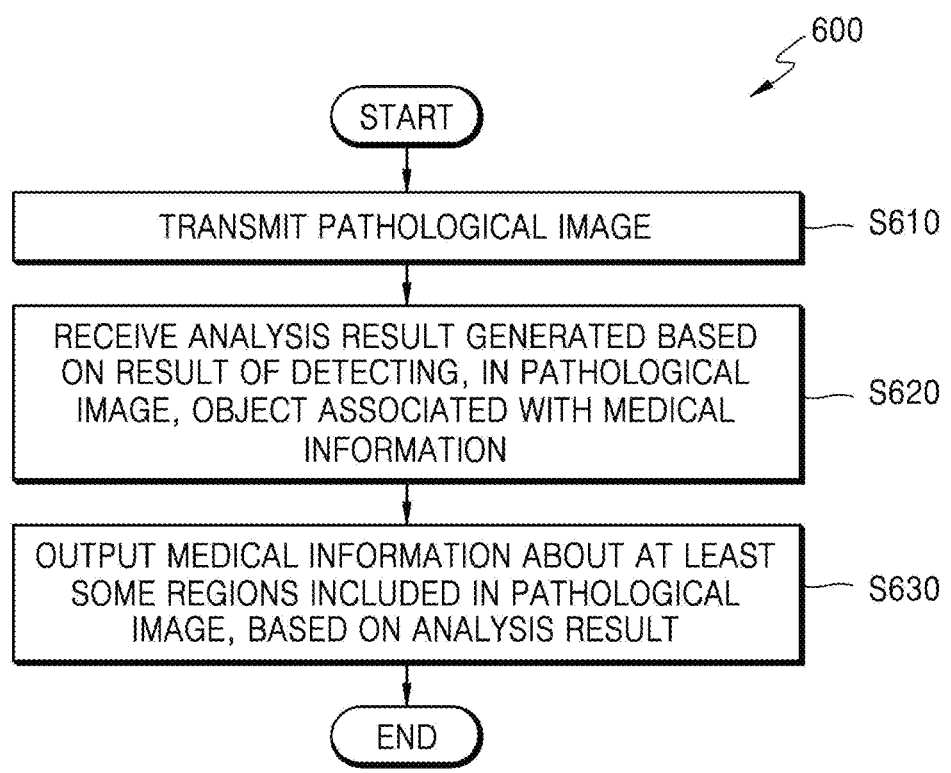
FIG. 6 is a flowchart illustrating an example of a method of analyzing a pathological image according to another embodiment of the present disclosure.

FIG. 6 is a flowchart illustrating an example of a method 600 of analyzing a pathological image according to another embodiment of the present disclosure. The method 600 may be initiated when a processor (e.g., at least one processor of a user terminal) transmits a pathological image (S610). Then, the processor may receive an analysis result generated based on a result of detecting, in the pathological image, an object associated with medical information (S620).

Then, the processor may output medical information about at least some regions included in the pathological image, based on the analysis result (S630). According to an embodiment, the at least some regions, the medical information about which is to be output, may include a region set by the processor, a region set based on a user input, a region obtained by modifying, based on a user input, a region set by the processor, or a region obtained by modifying, by the processor, a region set based on a user input.

In an embodiment, the processor may output at least one of information related to the level of PD-L1 expression in the at least some regions included in the pathological image or information related to the level of PD-L1 expression in one or more sub-regions included in the at least some regions. For example, at least one of whether cells included in the at least some regions or one or more sub-regions express PD-L1, the number of PD-L1 positive tumor cells, the number of PD-L1 negative tumor cells, the total number of tumor cells, the number of PD-L1 positive lymphocytes, the number of PD-L1 positive macrophages, the level of PD-L1 expression in the at least some regions, or the level of PD-L1 expression in one or more sub-regions may be output. The medical information may be displayed or output in various ways such as figures, colors, textures, layers, statistical methods, numerical values, text, etc.

According to an embodiment, the processor may output whether cells included in the at least some regions or one or more sub-regions express PD-L1. For example, the processor may output PD-L1 positive tumor cells in association with color information corresponding to positivity, and output PD-L1 negative tumor cells in association with color information corresponding to negativity.

According to an embodiment, when outputting the level of PD-L1 expression of one or more sub-regions, the processor may output the level of PD-L1 expression in association with color information corresponding to a numerical value indicating the level of PD-L1 expression of one or more sub-regions, at the center of each sub-region. For example, in a case in which the level of PD-L1 expression of a particular circular sub-region is 40%, the central portion of the sub-region may be output in a color corresponding to 40%.

According to an embodiment, the processor may output, for a sub-region associated with a cursor (i.e., an indicator of an input position on a display) displayed on the pathological image, at least one of the corresponding sub-region, the level of PD-L1 expression in the corresponding sub-region, the number of PD-L1 positive tumor cells, the number of PD-L1 negative tumor cells, or the total number of tumor cells included in the corresponding sub-region. Here, the sub-region associated with the cursor may be a circular sub-region centered on the cursor. The size of the circular sub-region may be set to have a size and/or a shape identical or similar to a region viewed by pathologists observing the pathological slide with an actual microscope.

According to an embodiment, the processor may output information related to the level of PD-L1 expression of only a region that satisfies a predefined criterion. For example, in a case in which at least one of at least some regions included in the pathological image, a plurality of sub-regions included in the at least some regions, or the sub-region associated with the cursor displayed on the pathological image is satisfies the predefined criterion, the processor may output information related to the level of PD-L1 expression in the region that satisfies the criterion. Here, the predefined criterion may be a criterion associated with at least one of the number of tumor cells, the size of a region occupied by tumor cells, or the range of the region occupied by the tumor cells.

The flowcharts illustrated in FIGS. 5 and 6 and the above descriptions thereof are only examples, and may be implemented in various ways. For example, one or more operations may be added or omitted, the order of operations may be changed, or at least some operations may overlap.

Figure 7:
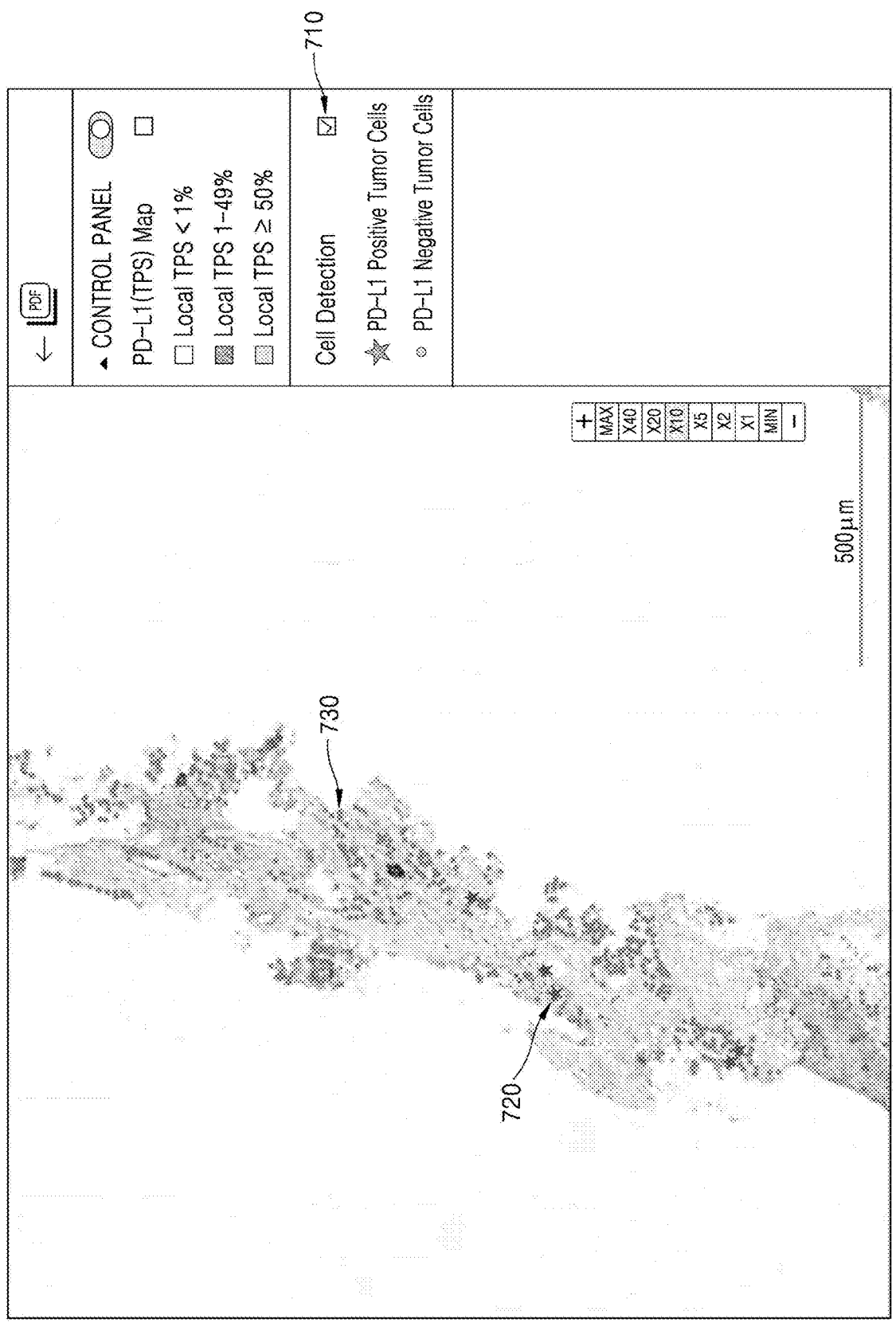
FIG. 7 illustrates an example of outputting cells detected in at least some regions of a pathological image, according to an embodiment of the present disclosure.

FIG. 7 illustrates an example of outputting cells detected in at least some regions of a pathological image, according to an embodiment of the present disclosure. According to an embodiment, the information processing system may detect an object associated with medical information in a pathological image by using a machine learning model. For example, the information processing system may detect, in a stained pathological image, positive cells that express a biomarker of interest, and negative cells that do not express the biomarker of interest. The objects detected as described above may be output through an output device of a user terminal.

FIG. 7 illustrates an example in which PD-L1 positive tumor cells 720 and PD-L1 negative tumor cells 730 detected in at least some regions of a pathological image are output to a display of a user terminal. According to an embodiment, in a case in which a user enables cell output by checking a cell detection check box 710 displayed on the display of the user terminal, cells included in the at least some regions included in the image and whether the cells express PD-L1 may be output. For example, as illustrated in FIG. 7, a layer displaying the detected PD-L1 positive tumor cells 720 and PD-L1 negative tumor cells 730 may be added on the pathological image. FIG. 7 illustrates that a partial region included in the pathological image and cells detected in the region are output at 10× magnification, however, when the user moves the output region through a user input or adjusts the output magnification, various regions may be output at various magnifications.

According to an embodiment, the user terminal may output the PD-L1 expression on cells such that the PD-L1 positive tumor cells 720 and the PD-L1 negative tumor cells 730 are distinguished from each other. For example, the user terminal may output the PD-L1 positive tumor cells 720 and the PD-L1 negative tumor cells 730 in different shapes. As a specific example, as illustrated in FIG. 7, the PD-L1 positive tumor cells 720 may be output as star-shaped dots corresponding to positivity, and the PD-L1 negative tumor cells 730 may be output as circular dots corresponding to negative.

As another example, the user terminal may output the PD-L1 positive tumor cells 720 and the PD-L1 negative tumor cells 730 in different colors. As a specific example, the PD-L1 positive tumor cells 720 may be output in purple corresponding to positivity, and the PD-L1 negative tumor cells 730 may be output in blue corresponding to negativity.

Although FIG. 7 illustrates an example of outputting whether tumor cells express PD-L1, but the present disclosure is not limited thereto, and various types of objects (e.g., positive cells that express a biomarker of interest, negative cells that do not express the biomarker of interest, etc.) detected in the pathological image may be output to the output device of the user terminal. With the above-described configuration, the user may easily check various types of objects detected in the pathological image, and easily check or derive relevant medical information therefrom.

Figure 8:
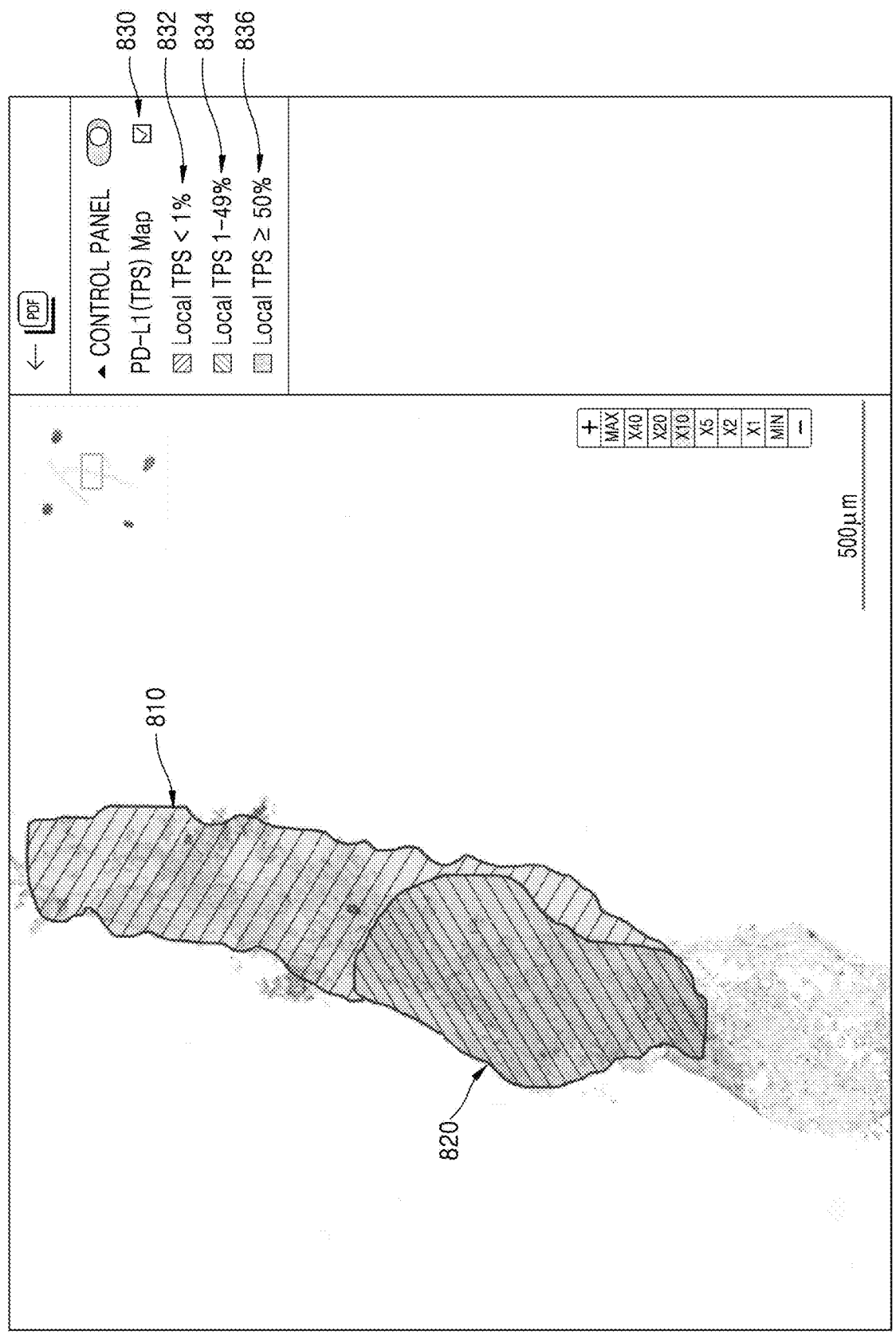
FIGS. 8 to 10 illustrate examples of visualizing and outputting tumor proportion score (TPS) values calculated based on information about programmed death-ligand 1 (PD-L1) expression on cells detected in a pathological image, according to an embodiment of the present disclosure.
Figure 9:
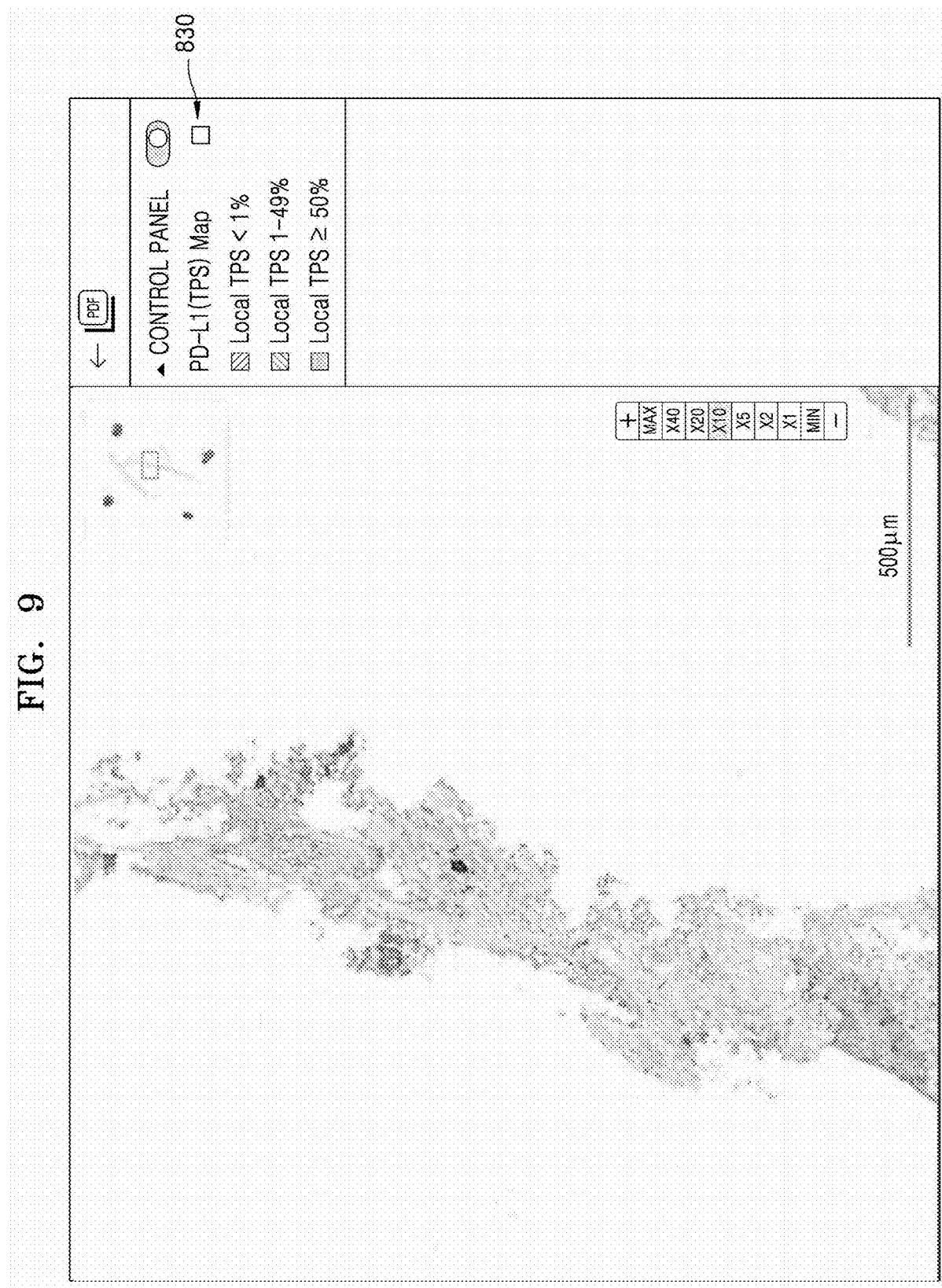
Figure 10:
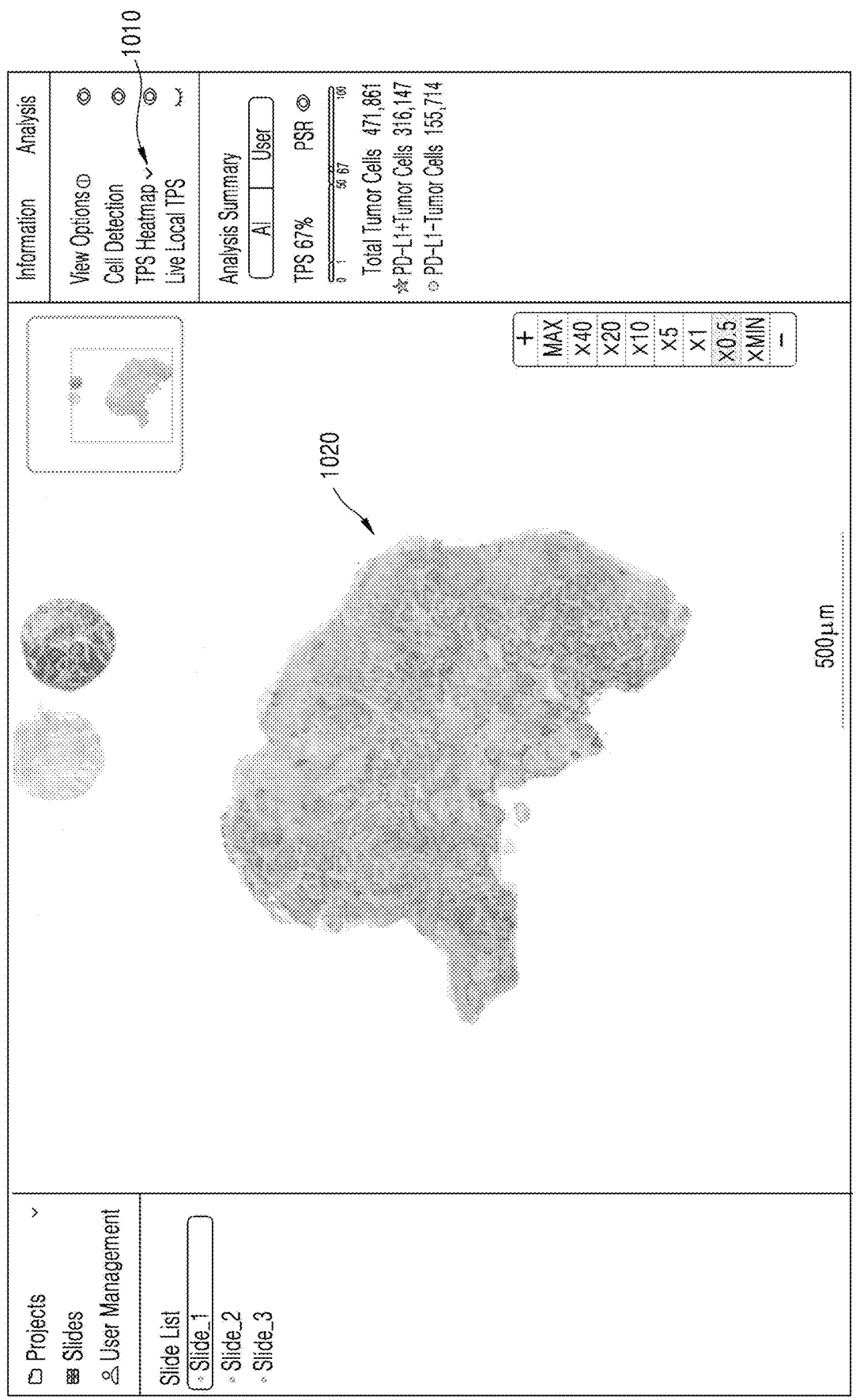

FIGS. 8 to 10 illustrate examples of visualizing and outputting TPS values calculated based on information about PD-L1 expression on cells detected in a pathological image, according to an embodiment of the present disclosure. According to an embodiment, the information processing system may divide the entire region or at least some regions of the pathological image into a plurality of sub-regions, and calculate various numerical values associated with medical information for one or more sub-regions. For example, the information processing system may divide the entire region or at least some regions of the pathological image into a plurality of circular sub-regions having the same size, and calculate the level of PD-L1 expression (e.g., a sub-TPS, a sub-CPS, etc.) in one or more sub-regions. Here, the circular sub-regions may be set to have the same shape and/or size as a region viewed by pathologists observing the pathological slide with an actual microscope. Also, the plurality of sub-regions may overlap. Various numerical values associated with medical information that are calculated in this way may be visualized and output through the output device of the user terminal.

FIG. 8 illustrates an example of visualizing and outputting a sub-TPS value calculated based on information about PD-L1 expression on cells detected in a pathological image, according to an embodiment of the present disclosure. FIG. 8 illustrates that some regions included in the pathological image are output at 10× magnification, however, when the user moves the output region through a user input or adjusts the output magnification, various regions may be output at various magnifications. In a case in which the user enables TPS map output by checking a TPS map check box 830 displayed on the display of the user terminal, a sub-TPS value for each of a plurality of sub-regions included in the pathological image may visualized and output. For example, a TPS map layer in which a sub-TPS value for each of the plurality of sub-regions is expressed in color may be added on the pathological image. The sub-TPS values may be associated with different colors depending on the range to which they belong. For example, sub-TPS<1% (832) may correspond to blue, 1%≤sub-TPS<50% (834) may correspond to green, and sub-TPS≥50% (836) may correspond to red. FIG. 8 illustrates a TPS map represented by shading and hatching, however, according to another embodiment, as described above, a TPS map represented by colors corresponding to the ranges to which the sub-TPS values belong, respectively, may be output.

According to an embodiment, a color indicating a particular point in the TPS map layer may represent a sub-TPS value of a sub-region associated with the point. For example, in a case in which a first point 810 is displayed in blue, this may indicate that a sub-TPS value for a circular sub-region having a certain size centered on the first point 810 is less than 1%. For example, in a case in which a second point 820 is displayed in green, this may indicate that a sub-TPS value for a circular sub-region having a certain size centered on the second point 820 is greater than or equal to 1% and less than 50%.

Meanwhile, in order to calculate a clinically significant level of PD-L1 expression (e.g., a TPS), it may be desirable that a sufficient number of tumor cells is present or the size or range of a region occupied by tumor cells satisfies a predefined criterion. That is, even within the pathological image, the level of PD-L1 expression in a region in which the number of tumor cells and the size or range of a region occupied by tumor cells satisfy a certain level may be considered valid. For example, the predefined criterion may be at least 100 tumor cells'. However, the predefined criterion is not limited thereto, and may vary depending on the type of PD-L1 antibody used for IHC staining.

According to an embodiment, the information processing system may calculate the level of PD-L1 expression only for a region that satisfies the predefined criterion, and the user terminal may output the level of PD-L1 expression only for the region that satisfies the predefined criterion. Referring to FIG. 8, there are points that are not shaded or hatched on the TPS map, which means that the sub-region associated with the points is determined as not satisfying the predefined criterion (e.g., a region in which the number of tumor cells is less than 100), and thus, the level of PD-L1 expression in the region is not output.

According to an embodiment, the user may disable the TPS map output by unchecking the TPS map check box 830. In a case in which the user disables the TPS map output, as illustrated in FIG. 9, the TPS map layer may be removed and only the pathological image may be output.

According to an embodiment, the user may change the shape of the TPS map to the shape of a heat map 1020 through a TPS map shape selection menu 1010. In a case in which the user changes the shape of the TPS map to the shape of the heat map 1020, the TPS map may be output in the shape of the heat map 1020 as illustrated in FIG. 10. While the TPS map according to the cut-off described above with reference to FIG. 8 is output with colors, shades, hatched lines, etc. corresponding to the ranges to which the sub-TPS values belong, the heat map 1020 may be output such that the output colors, the brightness of shades, etc. continuously change as the TPS value continuously changes. For example, the shade may become darker as the TPS value increases toward 100%, and the shade may become brighter as the TPS value decreases toward 0%. That is, the brightness (or darkness) of the output shade may change as the TPS value changes between 0% and 100%. As another example, the color may become redder as the TPS value increases toward 100%, and the color may become bluer as the TPS value decreases toward 0%. That is, the output color may change as the TPS value changes between 0% and 100%.

Figure 11:
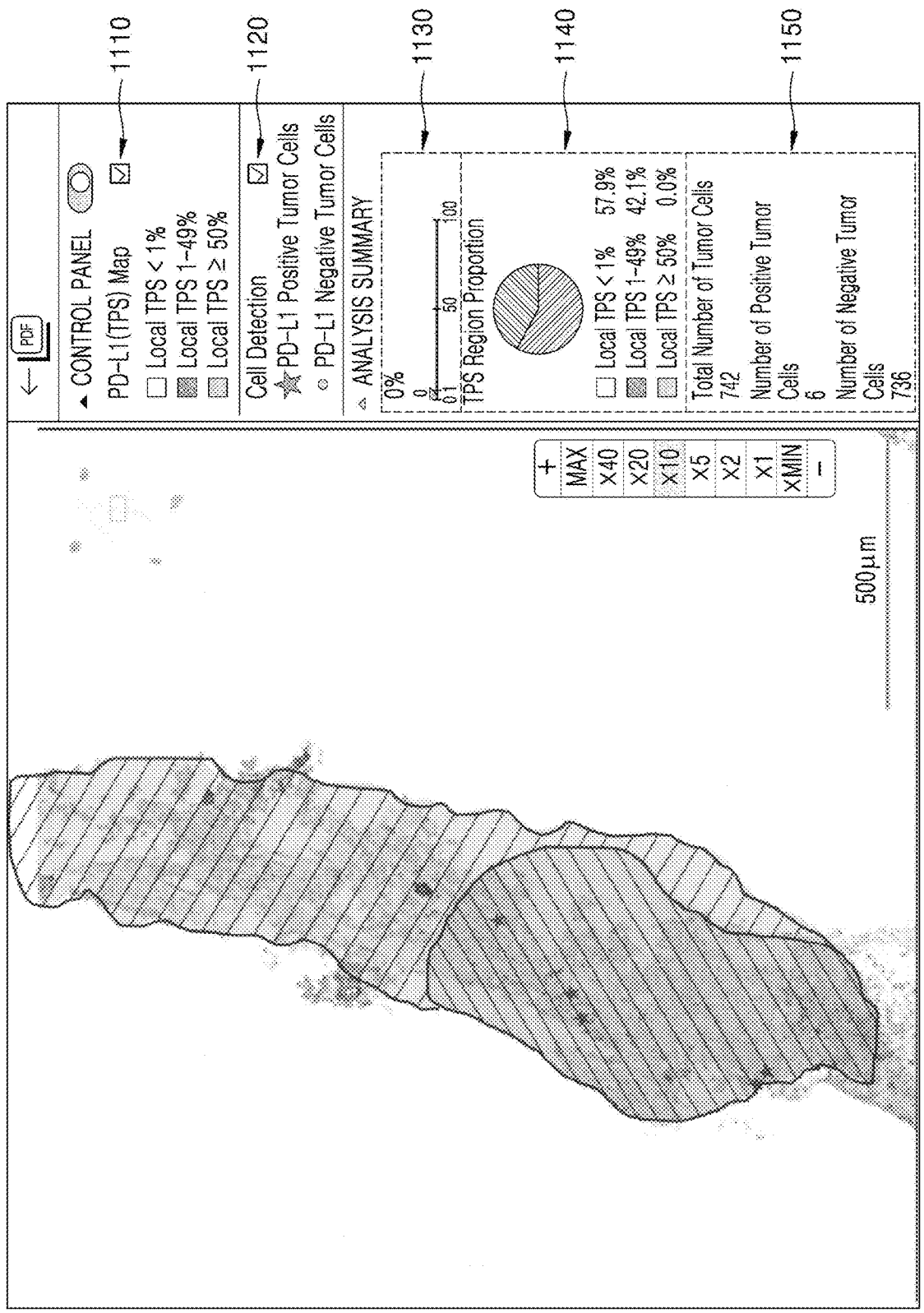
FIG. 11 is a diagram illustrating an example of outputting information related to PD-L1 expression derived from a pathological image, according to an embodiment of the present disclosure.

FIG. 11 is a diagram illustrating an example of outputting information related to PD-L1 expression derived from a pathological image, according to an embodiment of the present disclosure. According to an embodiment, the user may enable both cell output and TPS map output by checking both a TPS map check box 1110 and a cell detection check box 1120. In this case, a TPS map layer and a cell detection layer may be added on the pathological image such that a TPS map and detected cells are simultaneously output.

According to an embodiment, statistical information about various numerical values related to PD-L1 expression in the entire region or at least some regions of the pathological image may be provided. For example, a level 1130 of PD-L1 expression (e.g., a TPS, a CPS, etc.) in the entire region or at least some regions (e.g., a region displayed on the display of the user terminal, a region set by a machine learning model and/or a user, etc.) of the pathological image may be calculated and output through the output device of the user terminal. Here, in a case in which it is determined that the number of tumor cells present in the obtained pathological image of the patient is not sufficient to calculate a clinically significant level of PD-L1 expression, the user terminal may output an indication that the corresponding slide image is not suitable for analysis or an indication that another pathological slide of the patient is required. As another example, statistical data 1140 on the level of PD-L1 expression (e.g., a sub-TPS, a sub-CPS, etc.) calculated for one or more sub-regions included in the pathological image may be output through the output device of the user terminal. As another example, the number 1150 of tumor cells (e.g., the total number of tumor cells, the number of PD-L1 positive tumor cells, the number of PD-L1 positive tumor cells, etc.) included in the entire region or at least some regions of the pathological image may be output through the output device of the user terminal.

Figure 12:
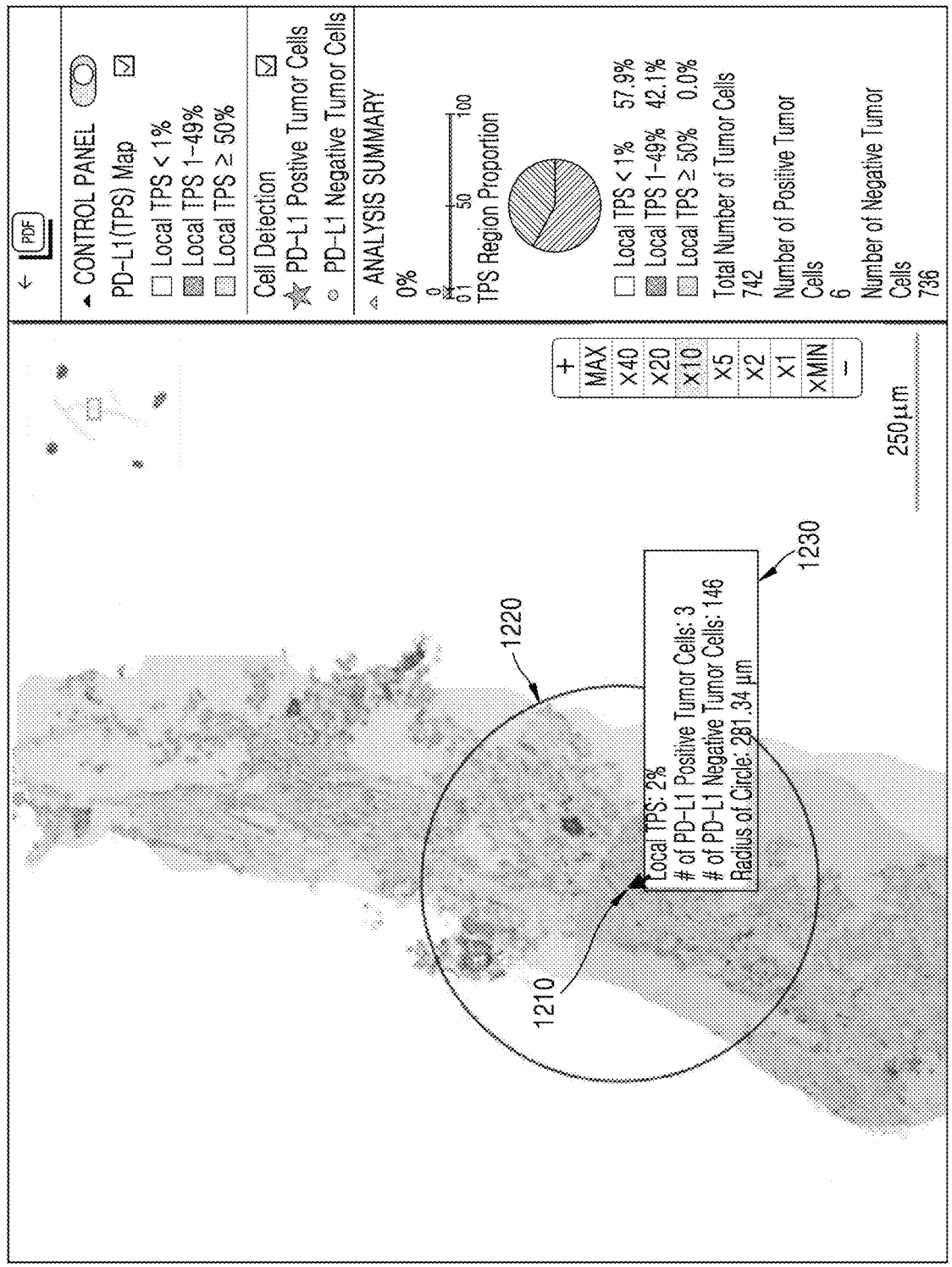
FIGS. 12 and 13 are diagrams illustrating examples of outputting information related to PD-L1 expression in sub-regions associated with cursors displayed on pathological images, respectively, according to an embodiment of the present disclosure.
Figure 13:
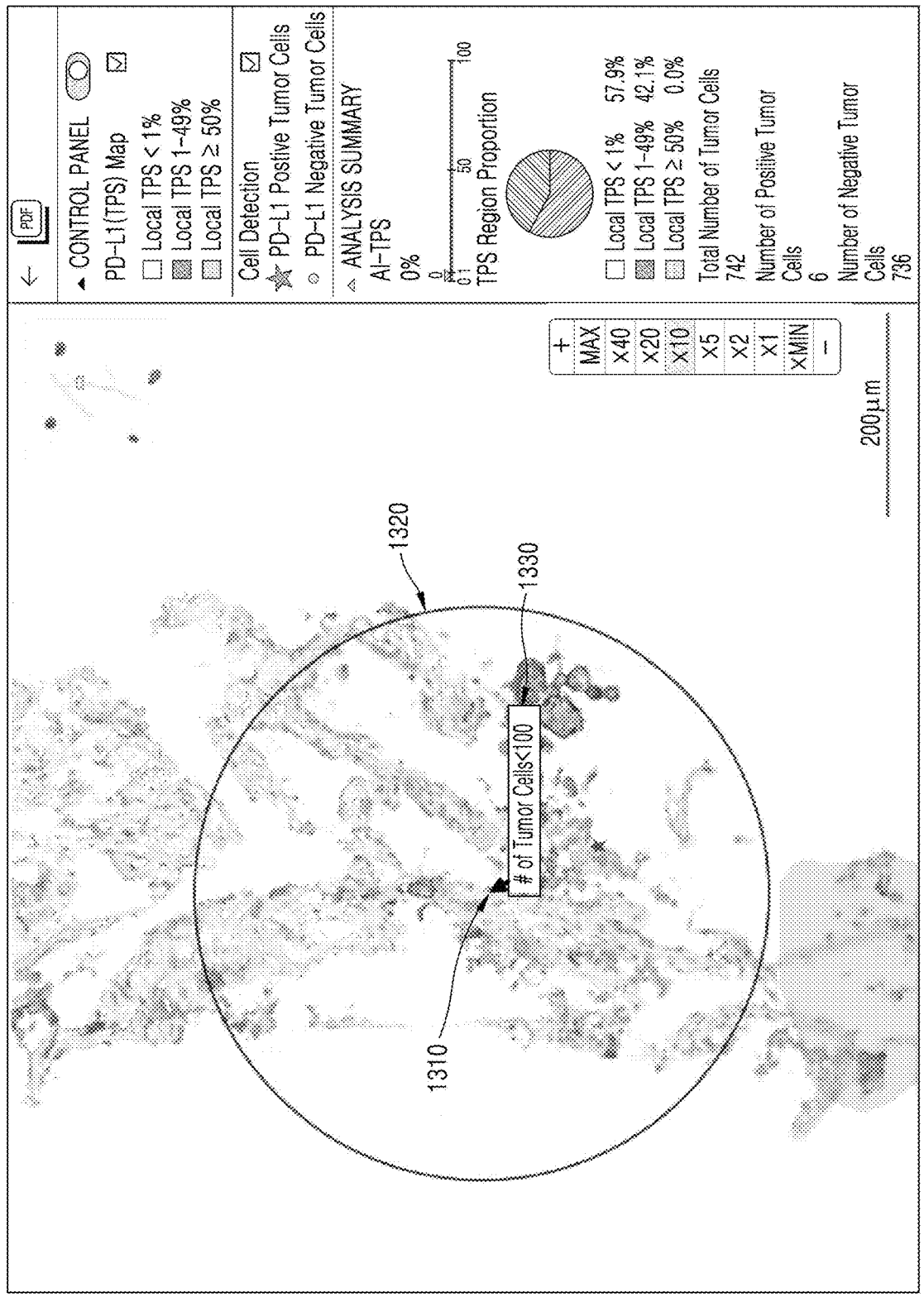

FIGS. 12 and 13 are diagrams illustrating examples of outputting information related to PD-L1 expression in sub-regions 1220 and 1320 associated with cursors 1210 and 1310 displayed on pathological images, respectively, according to an embodiment of the present disclosure. According to an embodiment, for the sub-region 1220 associated with the cursor 1210 (i.e., an indicator of an input position on a display) displayed on the pathological image, the terminal may output information about the sub-region and information 1230 related to PD-L1 expression in the sub-region. For example, as illustrated in FIG. 12, for the circular sub-region 1220 having a certain size centered on the position of the cursor 1210, the user terminal may output the boundary of the sub-region, the radius of the sub-region, a sub-TPS corresponding to the sub-region, the number of PD-L1 positive tumor cells, the number of PD-L1 negative tumor cells, the total number of tumor cells included in the location region, etc. Here, the circular sub-region 1220 centered on the position of the cursor 1210 may have the same shape and/or size as a region viewed by pathologists observing the pathological slide with an actual microscope. Through such a configuration, the user may observe the pathological image in an environment similar to that in observing an actual pathological slide with a microscope, and thus, usability may be improved.

According to an embodiment, in a case in which it is determined that a sufficient number (e.g., 100 or more) of tumor cells to calculate a clinically significant level of PD-L1 expression are not present in a particular sub-region, the level of PD-L1 expression in the region may not be output. For example, as illustrated in FIG. 13, in a case in which a total of less than 100 tumor cells are detected in the circular sub-region 1320 having a certain size centered on the position of the cursor 1310, the user terminal may output a message 1330 indicating that the total number of tumor cells in the sub-region is less than 100, without outputting the level of PD-L1 expression in the sub-region.

Figure 14:
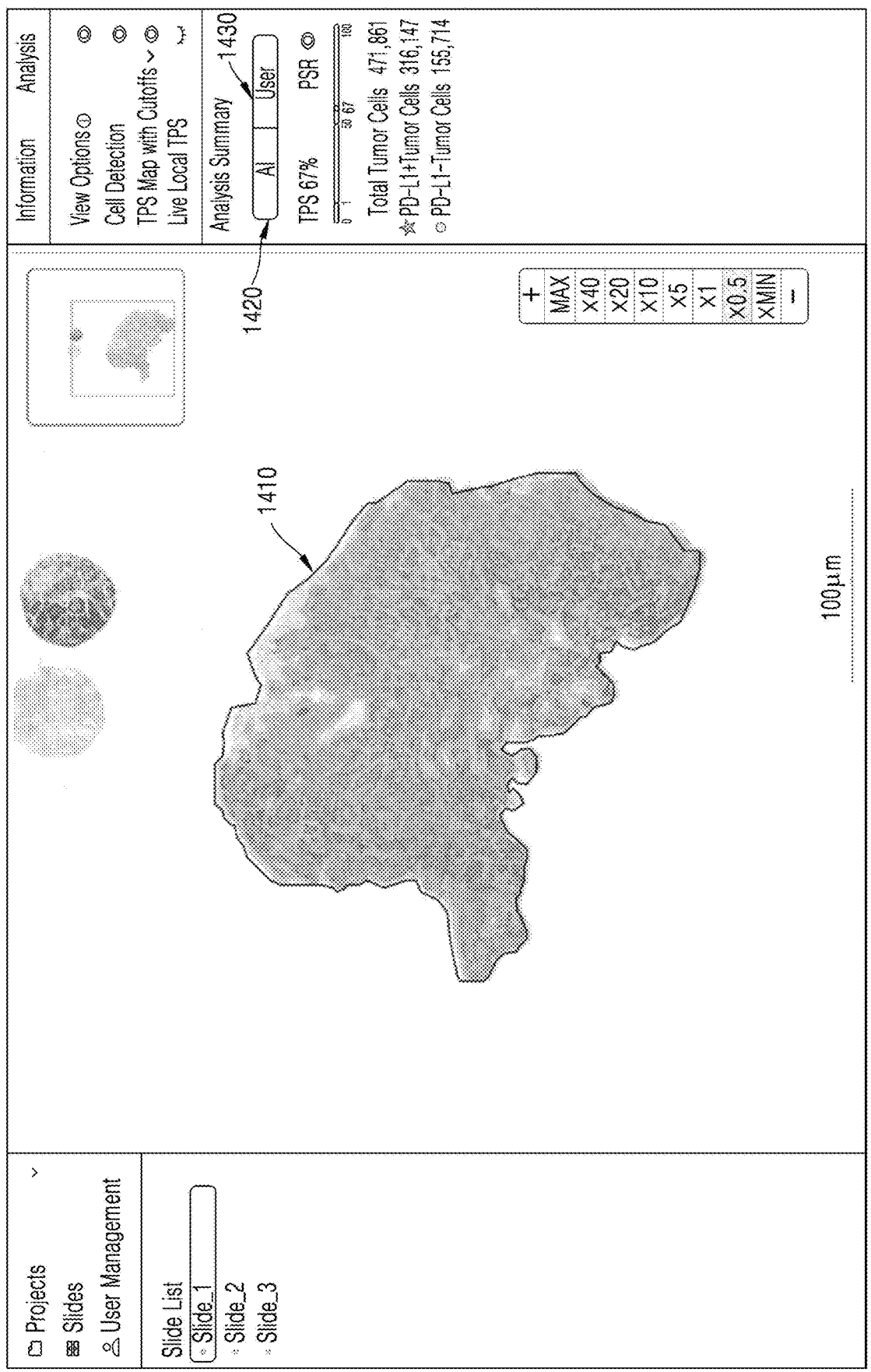
FIG. 14 is a diagram illustrating an example of outputting a region to be analyzed in a pathological image, according to an embodiment of the present disclosure.

FIG. 14 is a diagram illustrating an example of outputting a region 1410 to be analyzed in a pathological image, according to an embodiment of the present disclosure. The region 1410 to be analyzed in the pathological image may be set by a machine learning model and/or a user. For example, in a case in which the user selects an AI button 1420, the information processing system may set the region 1410 to be analyzed in the pathological image, by using the machine learning model. Here, the machine learning model may be a model trained to receive a pathological image and infer the region 1410 to be analyzed in the pathological image. The region 1410 to be analyzed that is inferred by the machine learning model may be output through an output device of a user terminal.

As another example, when the user selects a User button 1430, the region 1410 to be analyzed may be set based on an input of the user. For example, the region 1410 to be analyzed may be set by the user selecting at least a partial region of the pathological image. As another example, when the user selects at least a partial region of the pathological image, the information processing system or the user terminal may modify the at least a partial region selected by the user, based on information related to tissues and/or structures in the human body included in the pathological image, and the modified region (e.g., a region obtained by modifying the at least a partial region selected by the user such that the contour of the region to be analyzed is the same as or similar to the contour of a tissue region and/or a structure region in the human body) may be finally set as the region 1410 to be analyzed. As another example, the region 1410 to be analyzed may be a region modified by the user based on the region that is inferred by the machine learning model. In detail, the region to be analyzed that is inferred by the machine learning model may be transmitted to the user terminal, and then displayed on a screen of the user terminal, and the user may modify at least a part of the inferred region to be analyzed. The region modified by the user may be finally set as the region 1410 to be analyzed. The information processing system may generate an analysis result on the region 1410 to be analyzed, and provide the analysis result to the user terminal.

FIGS. 15 to 18 are diagrams showing that predictive performance for responsiveness to immuno-oncology therapy is improved when a method of analyzing a pathological image according to an embodiment of the present disclosure is applied. In general, it may be predicted that, as the level of PD-L1 expression increases (i.e., as a TPS or a CPS increases), the responsiveness to immuno-oncology therapy is better, and it may be predicted that, as the level of PD-L1 expression increases (i.e., as a TPS or a CPS decreases), the responsiveness to immuno-oncology therapy is worse. Therefore, it may be estimated that, for patients grouped into a patient group with a TPS greater than a cut-off value, which is a certain TPS value, and a patient group with a TPS less than the cut-off value, as the difference in responsiveness to immuno-oncology therapy between the two groups increases, the predictive performance for responsiveness to immuno-oncology therapy is better. In the graphs in FIGS. 15 to 18, the horizontal axis represents progression-free survival (PFS), and the vertical axis represents survival rate.

Figure 15:
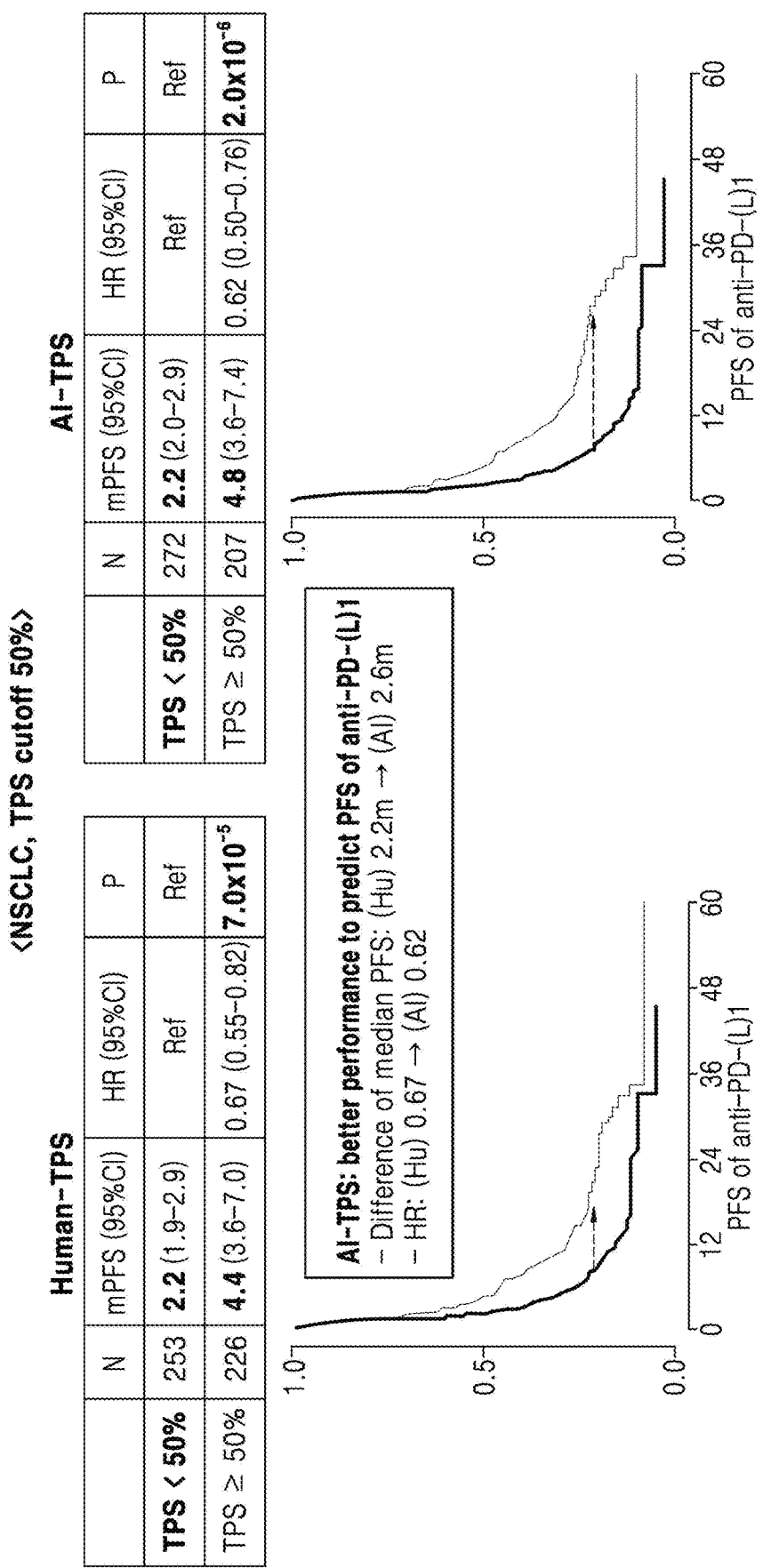
FIGS. 15 to 18 are diagrams showing that predictive performance for responsiveness to immuno-oncology therapy is improved when a method of analyzing a pathological image according to an embodiment of the present disclosure is applied.

FIG. 15 illustrates an example of comparing, based on PFS, predictive performance for responsiveness to immuno-oncology therapy on pathological images of non-small cell lung cancer (NSCLC) patients, between a patient group classified by applying the method of analyzing a pathological image according to an embodiment of the present disclosure, and a patient group classified by a pathologist, with a TPS cut-off value of 50%. Referring to FIG. 15, the difference between the median of PFS of the patient group determined by the pathologist to be less than 50% in TPS and the median of PFS of the patient group determined to be greater than or equal to 50% in TPS is 2.2 months. On the other hand, the difference between the median of PFS of the patient group determined by the method of analyzing a pathological image according to an embodiment of the present disclosure to be less than 50% in TPS and the median of PFS of the patient group determined to be greater than or equal to 50% in TPS is 2.6 months. That is, it may be confirmed that, in a case of determining according to an embodiment of the present disclosure, the difference in responsiveness to immuno-oncology therapy between the two patient groups increases, and thus, the predictive performance for responsiveness to immuno-oncology therapy is improved.

Figure 16:
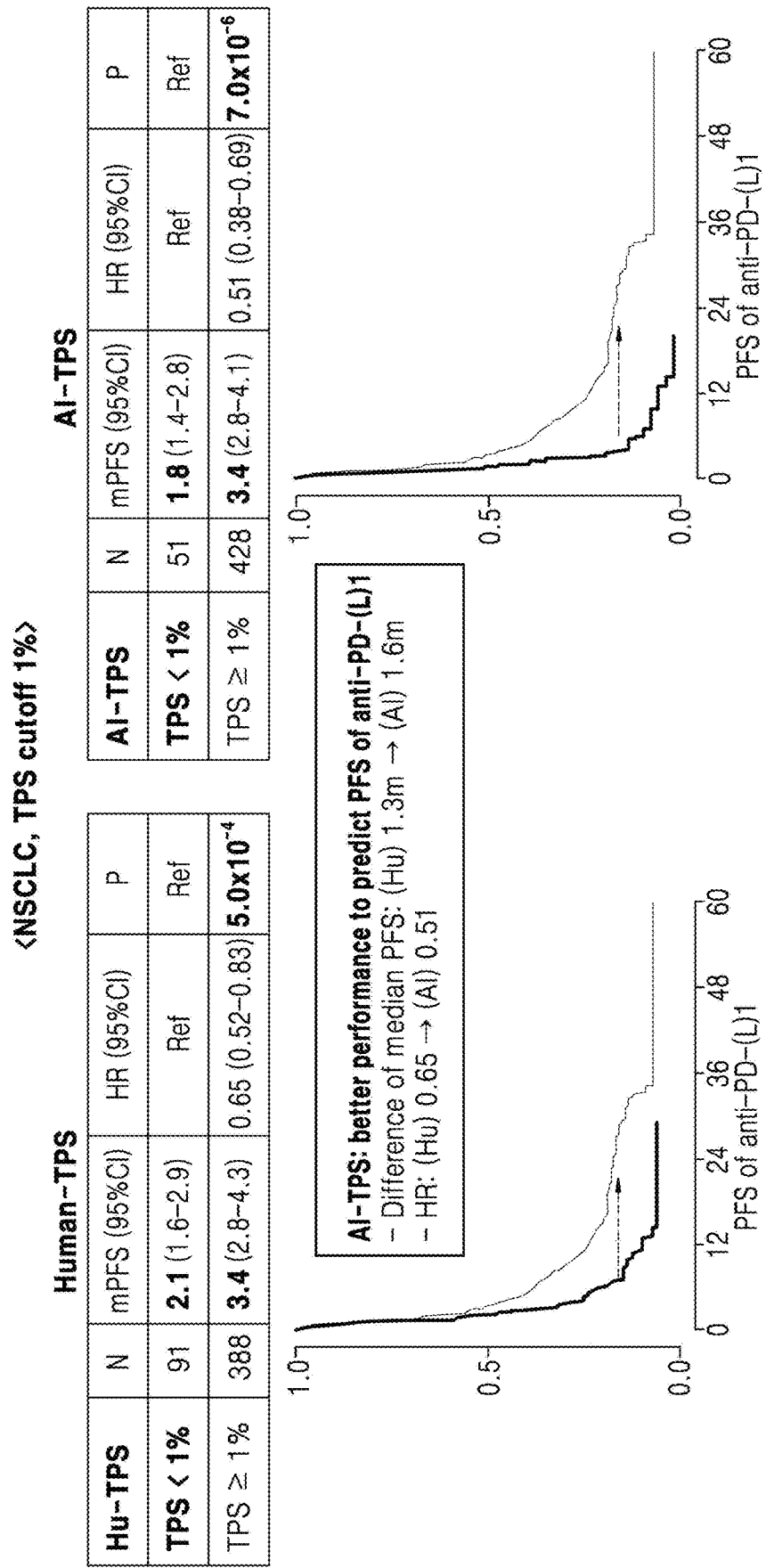

FIG. 16 is a diagram illustrating an example of comparing, based on PFS, predictive performance for responsiveness to immuno-oncology therapy on pathological images of NSCLC patients, between a patient group classified by applying, with a TPS cut-off value of 51%, the method of analyzing a pathological image according to an embodiment of the present disclosure, and a patient group classified by a pathologist. Referring to FIG. 16, the difference between the median of PFS of the patient group determined by the pathologist to be less than 1% in TPS and the median of PFS of the patient group determined to be greater than or equal to 1% in TPS is 1.3 months. On the other hand, the difference between the median of the patient group determined by the method of analyzing a pathological image according to an embodiment of the present disclosure to be less than 1% in TPS and the median of PFS of the patient group determined to be greater than or equal to 1% in TPS is 1.6 months. That is, even in a case of a TPS cut-off value of 1%, as in the case of a TPS cut-off value of 50%, it may be confirmed that the predictive performance for responsiveness to immuno-oncology therapy is improved by determining the TPS by applying the method according to an embodiment of the present disclosure.

Figure 17:
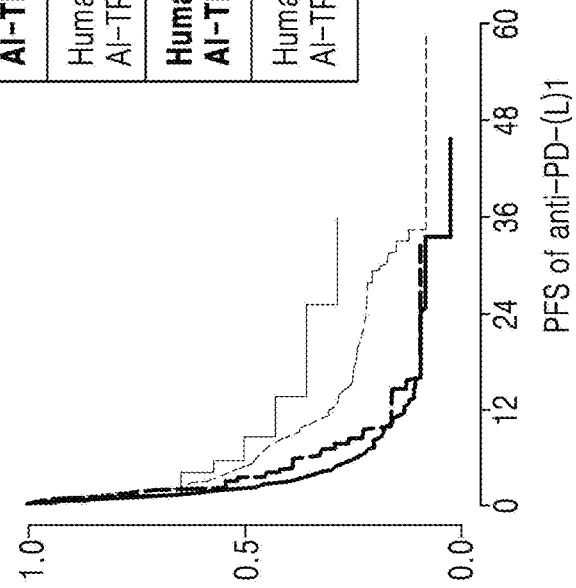

FIG. 17 illustrates an example of comparing, based on PFS, predictive performance for responsiveness to immuno-oncology therapy on pathological images of NSCLC patients, between four groups of patients classified by applying the method of analyzing a pathological image according to an embodiment of the present disclosure, and patients classified by a pathologist, with a TPS cut-off value of 50%. Referring to FIG. 17, it may be confirmed that, among 253 patients who are determined by the pathologist to be less than 50% in TPS, 14 patients (approximately 5.5%) are determined to be greater than or equal to 50% in TPS according to the method of analyzing a pathological image according to an embodiment of the present disclosure, and the median of their PFS is 6.8 months, indicating relatively excellent responsiveness to immuno-oncology therapy. That is, it may be confirmed that, according to the method of analyzing a pathological image according to an embodiment of the present disclosure, the predictive performance for responsiveness to immuno-oncology therapy is significantly improved by calculating an objective PD-L1 expression index, compared to determination by a doctor.

Figure 18:
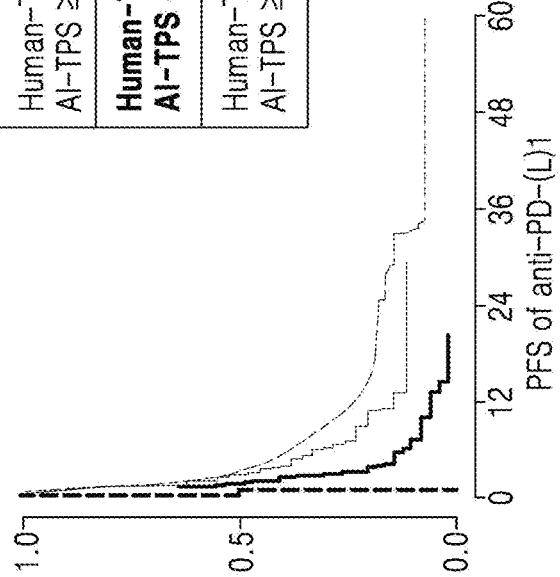

FIG. 18 illustrates an example of comparing, based on PFS, predictive performance for responsiveness to immuno-oncology therapy on pathological images of NSCLC patients, between four groups of patients classified by applying the method of analyzing a pathological image according to an embodiment of the present disclosure, and patients classified by a pathologist, with a TPS cut-off value of 1%. Referring to FIG. 18, it may be confirmed that, among 91 patients who are determined by the pathologist to be less than 1% in TPS, 42 patients (approximately 46.2%) are determined to be greater than or equal to 1% in TPS according to the method of analyzing a pathological image according to an embodiment of the present disclosure, and the median of their PFS is 2.9 months, indicating relatively good responsiveness to immuno-oncology therapy. That is, even in a case of a TPS cut-off value of 1%, as in the case of a TPS cut-off value of 50%, it may be confirmed that the predictive performance for responsiveness to immuno-oncology therapy is improved by determining the TPS by applying the method according to an embodiment of the present disclosure.

Figure 19:
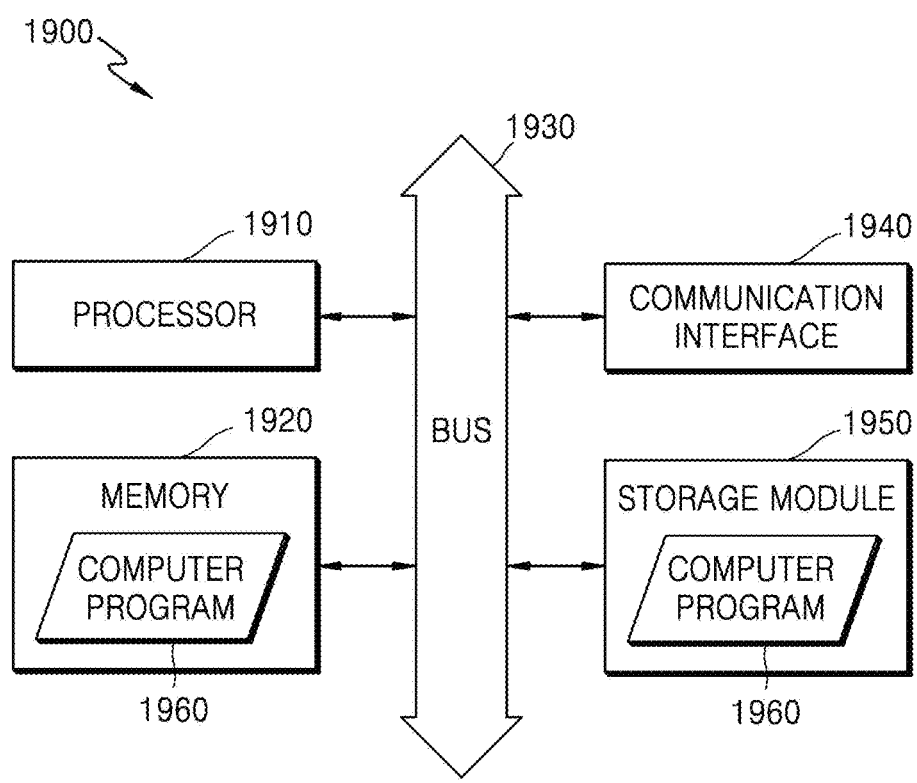
FIG. 19 is a configuration diagram of an arbitrary computing device associated with a method of analyzing a pathological image according to an embodiment of the present disclosure.

FIG. 19 is a configuration diagram of an arbitrary computing device 1900 associated with a method of analyzing a pathological image according to an embodiment of the present disclosure. For example, the computing device 1900 may include an information processing system and/or a user terminal. As illustrated in FIG. 19, the computing device 1900 may include one or more processors 1910, a bus 1930, a communication interface 1940, a memory 1920 for loading a computer program 1960 to be executed by the processor 1910, and a storage module 1950 storing the computer program 1960. However, only components related to an embodiment of the present disclosure are illustrated in FIG. 19. Thus, those of skill in the art to which the present disclosure pertains may understand that other general-purpose components may be further included in addition to the components illustrated in FIG. 19.

The processors 1910 control the overall operation of each component of the computing device 1900. The processors 1910 may be configured to include a central processing unit (CPU), a microprocessor unit (MPU), a microcontroller unit (MCU), a graphics processing unit (GPU), or any type of processor well known in the technical field of the present disclosure. In addition, the processors 1910 may perform an arithmetic operation on at least one application or program for executing the method according to the embodiments of the present disclosure. The computing device 1900 may include one or more processors.

The memory 1920 may store various types of data, commands, and/or information. The memory 1920 may load one or more computer programs 1960 from the storage module 1950 to execute the method/operation according to various embodiments of the present disclosure. The memory 1920 may be implemented as a volatile memory such as RAM, but the technical scope of the present disclosure is not limited thereto.

The bus 1930 may provide a communication function between components of the computing device 1900. The bus 1930 may be implemented as various types of buses, such as an address bus, a data bus, a control bus, etc.

The communication interface 1940 may support wired and wireless Internet communication of the computing device 1900. In addition, the communication interface 1940 may support various communication methods in addition to the Internet communication. To this end, the communication interface 1940 may be configured to include a communication module well known in the technical field of the present disclosure.

The storage module 1950 may non-temporarily store one or more computer programs 1960. The storage module 1950 may be configured to include a non-volatile memory such as ROM, EPROM, EEPROM, flash memory, etc., a hard disk, a detachable disk, or any type of computer-readable recording medium well known in the art to which the present disclosure pertains.

The computer program 1960 may include one or more instructions that, when loaded into the memory 1920, cause the processors 1910 to perform an operation/method according to various embodiments of the present disclosure. That is, the processors 1910 may perform operations/methods according to various embodiments of the present disclosure by executing the one or more instructions.

For example, the computer program 1960 may include one or more instructions for receiving a pathological image, generating an analysis result on the pathological image by using a machine learning model, and outputting, based on the analysis result, medical information about at least some regions included in the pathological image. In this case, the computer program 1960 may include instructions for detecting an object associated with medical information in a received medical image. In addition, the computer program 1960 may include instructions for calculating a level of biomarker expression in at least some regions included in a pathological image. In addition, the computer program 1960 may include instructions for outputting an analysis result and/or medical information including a level of biomarker expression.

The above description of the present disclosure is provided to enable those of skill in the art to perform or use the present disclosure. Various modifications of the present disclosure will be readily apparent to those of skill in the art, and the general principles defined herein may be applied to various modifications without departing from the spirit or scope of the present disclosure. Thus, the present disclosure is not intended to be limited to the examples described herein, but is intended to be accorded the broadest scope consistent with the principles and novel features disclosed herein.

Although example implementations may refer to utilizing aspects of the presently disclosed subject matter in the context of one or more standalone computer systems, the subject matter is not so limited, and they may be implemented in conjunction with any computing environment, such as a network or distributed computing environment. Furthermore, aspects of the presently disclosed subject matter may be implemented in or across a plurality of processing chips or devices, and storage may be similarly influenced across a plurality of devices. Such devices may include PCs, network servers, and handheld devices.

Although the present disclosure has been described in connection with some embodiments herein, it should be understood that various modifications and changes can be made without departing from the scope of the present disclosure, which may be understood by those of skill in the art to which the present disclosure pertains. In addition, such modifications and changes should be considered within the scope of the claims appended herein.

The invention claimed is:

1. A method, performed by at least one processor of an information processing system of analyzing a pathological image, the method comprising:
    receiving a pathological image;
    detecting an object in the pathological image, by using a machine learning model, wherein the machine learning model is trained to detect at least one of a PD-L1 (programmed deathligand1) positive tumor cell, a PD-L1 negative tumor cell, a PD-L1 positive lymphocyte, or a PD-L1 positive macrophage;
    receiving a user input for setting a location of a region of interest (ROI) to be analyzed on the pathological image being displayed on a display;
    generating an analysis result in the ROI based on a result of the detecting, wherein the analysis result includes a level of PD-L1 expression on cells in the ROI; and
    displaying medical information about the ROI on the display based on the analysis result, wherein the medical information includes at least one of a tumor proportion score (TPS) or a combined positive score (CPS) corresponding to the ROI, a number of PD-L1 positive tumor cells included in one or more sub-regions of the ROI, or a number of PD-L1 negative tumor cells included in the one or more sub-regions of the ROI on the display.

2. The method of claim 1, wherein the ROI is set by receiving a user input for setting a region to be analyzed, or by modifying, based on a user input, a region set by the at least one processor.

3. The method of claim 1, wherein the object associated with the medical information comprises at least one of a tumor cell, an immune cell, or a cancer area.

4. The method of claim 1 further comprising receiving a user input enabling cell output by checking a cell detection check box displayed on the display of a user terminal, and displaying, to the display, PD-L1 positive tumor cells and PD-L1 negative tumor cells in different colors.

5. The method of claim 1, wherein the machine learning model is trained based on training pathological images of cells which are stained by immunohistochemistry (IHC) by using a PD-L1 antibody, and annotation information about PD-L1 expression on at least some cells in the training pathological images.

6. The method of claim 1, wherein the displaying comprises outputting the medical information to the display of a user terminal to display at least one of a boundary of the ROI, the TPS corresponding to the ROI, the CPS corresponding to the ROI, the number of PD-L1 positive tumor cells included in the ROI, and the number of PD-L1 negative tumor cells included in the ROI.

7. The method of claim 1, wherein
    the generating of the analysis result comprises calculating at least one of the TPS or the CPS based on the at least one of the PD-L1 positive tumor cell, the PD-L1 negative tumor cell, the PD-L1 positive lymphocyte, or the PD-L1 positive macrophage in the ROI.

8. The method of claim 1,
    wherein the generating of the analysis result comprises:
        identifying that a first ROI satisfies a predefined criterion; and
        generating the analysis result in the first ROI that satisfies the predefined criterion, and
    wherein the method further comprises:
        receiving a user input for setting a location of a second ROI on the pathological image;
        identifying that the second ROI does not satisfy the predefined criterion; and displaying information indicating that the second ROI does not satisfy the predefined criterion, without displaying medical information about the second ROI.

9. The method of claim 8, wherein the predefined criterion is associated with at least one of a number of tumor cells, a size of a region occupied by the tumor cells, or a range of the region occupied by the tumor cells.

10. A method, performed by at least one processor of a user terminal of processing a pathological image, the method comprising:
displaying a pathological image on a display of the user terminal;
receiving a user input for setting a location of a region of interest (ROI) to be analyzed on the pathological image;
receiving medical information about the ROI based on a result of detecting an object in the pathological image, wherein the object is detected by a machine learning model trained to detect at least one of a PD-L1 positive tumor cell, a PD-L1 negative tumor cell, a PD-L1 positive lymphocyte, or a PD-L1 positive macrophage;
generating an analysis result in the ROI based on the result of the detecting; and
displaying the medical information about the ROI on the display based on the analysis result, wherein the displayed medical information includes at least one of a tumor proportion score (TPS) or a combined positive score (CPS) corresponding to the ROI, a number of PD-L1 positive tumor cells included in one or more sub-regions of the ROI, or a number of PD-L1 negative tumor cells included in the one or more sub-regions of the ROI on the display.

11. The method of claim 10, wherein the displaying the medical information comprises displaying at least one of information related to a level of PD-L1 expression in the ROI or information related to the level of PD-L1 expression in the one or more sub-regions of the ROI.

12. The method of claim 10, wherein the displaying of the medical information comprises displaying at least one of whether cells included in the ROI express PD-L1, a total number of tumor cells included in the ROI, a number of PD-L1 positive lymphocytes included in the ROI, a number of PD-L1 positive macrophages included in the ROI, or a level of PD-L1 expression in the ROI.

13. The method of claim 10, wherein the displaying of the medical information further comprises displaying a cell detection check box for enabling cell output, and displaying PD-L1 positive tumor cells and PD-L1 negative tumor cells in different colors based on a user input checking the cell detection check box.

14. The method of claim 10, wherein the displaying of the medical information further comprises displaying at least one of whether cells included in the one or more sub-regions of the ROI express PD-L1, a total number of tumor cells included in the one or more sub-regions, a number of PD-L1 positive lymphocytes included in the one or more sub-regions, a number of PD-L1 positive macrophages included in the one or more sub-regions, or a level of PD-L1 expression in the one or more sub-regions.

15. The method of claim 10, wherein the displaying of the medical information further comprises displaying, at the one or more sub-regions of the ROI, a level of PD-L1 expression in the one or more sub-regions by using a color corresponding to a numerical value indicated by the level of PD-L1 expression.

16. The method of claim 10, wherein the displaying of the medical information comprises displaying at least one of a boundary of the ROI, the TPS corresponding to the ROI.

17. The method of claim 10, wherein the displaying of the medical information comprises:
displaying information related to a level of PD-L1 expression in the ROI that satisfies a predefined criterion.

18. The method of claim 10, wherein the TPS or the CPS is calculated based on the at least one of the PD-L1 positive tumor cell, the PD-L1 negative tumor cell, the PD-L1 positive lymphocyte, or the PD-L1 positive macrophage.

19. The method of claim 10, wherein the ROI is set by receiving a user input for setting a region to be analyzed, or by modifying, based on a user input, a region set by the at least one processor, or by modifying, by the at least one processor.

20. An information processing system comprising:
a memory; and
at least one processor connected to the memory and configured to execute at least one computer-readable program stored in the memory, wherein the at least one computer-readable program comprises instructions for:
receiving a pathological image;
detecting an object in the pathological image, by using a machine learning model, wherein the machine learning model is configured to detect at least one of a PD-L1 positive tumor cell, a PD-L1 negative tumor cell, a PD-L1 positive lymphocyte, or a PD-L1 positive macrophage;
receiving a user input for setting a location of a region of interest (ROI) to be analyzed on the pathological image being displayed on a display;
generating an analysis result in the ROI based on a result of the detecting, wherein the analysis result includes a level of PD-L1 expression on cells in the ROI; and
displaying medical information about the ROI on the display based on the analysis result, wherein the medical information includes at least one of a tumor proportion score (TPS) or a combined positive score (CPS) corresponding to the ROI, a number of PD-L1 positive tumor cells included in one or more sub-regions of the ROI, or a number of PD-L1 negative tumor cells included in the one or more sub-regions of the ROI on the display.

* * * * *